(12) United States Patent
Yamada et al.

(10) Patent No.: US 12,342,863 B2
(45) Date of Patent: *Jul. 1, 2025

(54) HEATER ASSEMBLY AND CONTAINER

(71) Applicant: JAPAN TOBACCO INC., Tokyo (JP)

(72) Inventors: Manabu Yamada, Tokyo (JP);
Manabu Takeuchi, Tokyo (JP);
Yasunobu Inoue, Tokyo (JP);
Kimitaka Uchii, Tokyo (JP); Tateki Sumii, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 35 days.

This patent is subject to a terminal disclaimer.

(21) Appl. No.: 18/448,649

(22) Filed: Aug. 11, 2023

(65) Prior Publication Data

US 2023/0389606 A1 Dec. 7, 2023

Related U.S. Application Data

(60) Continuation of application No. 18/109,110, filed on Feb. 13, 2023, now Pat. No. 11,805,813, which is a
(Continued)

(30) Foreign Application Priority Data

Apr. 26, 2018 (JP) .................................. 2018-085336

(51) Int. Cl.
*A24F 40/42* (2020.01)
*A24F 40/46* (2020.01)
(Continued)

(52) U.S. Cl.
CPC .............. *A24F 40/42* (2020.01); *A24F 40/46* (2020.01); *A24F 40/51* (2020.01); *A24F 40/53* (2020.01); *A24F 40/20* (2020.01)

(58) Field of Classification Search
None
See application file for complete search history.

(56) References Cited

U.S. PATENT DOCUMENTS 5,954,979 A 9/1999 Counts et al.
11,696,601 B2 * 7/2023 Yamada .................. A24F 40/46
131/329
(Continued)

FOREIGN PATENT DOCUMENTS

CN 104135879 A 11/2014
CN 205072071 U 3/2016
(Continued)

OTHER PUBLICATIONS

Chinese Office Action and Search Report for Chinese Application No. 201980028486.0, dated Apr. 27, 2023, with an English translation.
(Continued)

*Primary Examiner* — James Harvey
(74) *Attorney, Agent, or Firm* — Birch, Stewart, Kolasch & Birch, LLP

(57) ABSTRACT

A heater assembly comprises a container including a cylindrical portion that forms a chamber in which a flavor generating article is contained, and a heater arranged in a peripheral surface of the cylindrical portion. The container includes a first channel extending along a longitudinal direction of the cylindrical portion and located adjacently to the chamber in a direction intersecting with the longitudinal direction of the cylindrical portion, and a second channel extending through the chamber along the longitudinal direction of the cylindrical portion. The first channel is in communication with the second channel.

15 Claims, 24 Drawing Sheets

Related U.S. Application Data division of application No. 17/078,445, filed on Oct. 23, 2020, now Pat. No. 11,696,601, which is a continuation of application No. PCT/JP2019/017130, filed on Apr. 23, 2019.

(51) Int. Cl.
*A24F 40/51* (2020.01)
*A24F 40/53* (2020.01)
*A24F 40/20* (2020.01)

(56) References Cited

U.S. PATENT DOCUMENTS

| | | | |
|---|---|---|---|
| 11,696,681 B2* | 7/2023 | Felix | A61B 5/0031 600/302 |
| 11,805,813 B2* | 11/2023 | Yamada | A24F 40/53 |
| 2007/0102013 A1 | 5/2007 | Adams et al. | |
| 2014/0338686 A1 | 11/2014 | Plojoux et al. | |
| 2014/0366900 A1 | 12/2014 | Plojoux et al. | |
| 2016/0205998 A1 | 7/2016 | Matsumoto et al. | |
| 2017/0002583 A1 | 3/2017 | Blandino et al. | |
| 2020/0093178 A1* | 3/2020 | Serventi | B29C 63/0069 |
| 2020/0114095 A1 | 4/2020 | Holroyd et al. | |
| 2021/0045448 A1 | 2/2021 | Yamada et al. | |
| 2022/0346453 A1 | 11/2022 | Yamada et al. | |
| 2023/0389606 A1* | 12/2023 | Yamada | H05B 3/40 |
| 2024/0081408 A1* | 3/2024 | Yamada | A24F 40/46 |
| 2024/0164448 A1* | 5/2024 | Inoue | A24F 40/70 |

FOREIGN PATENT DOCUMENTS

| | | |
|---|---|---|
| CN | 206043448 U | 3/2017 |
| CN | 106690427 A | 5/2017 |
| CN | 107183789 A | 9/2017 |
| EP | 0 503 767 A1 | 9/1992 |
| EP | 3 610 741 A1 | 2/2020 |
| GB | 2534215 A | 7/2018 |
| JP | 5-115272 A | 5/1993 |
| JP | 6-46955 A | 2/1994 |
| JP | 8-511176 A | 11/1996 |
| JP | 2001-521123 A | 11/2001 |
| JP | 2009-509523 A | 3/2009 |
| JP | 2011-87569 A | 5/2011 |
| JP | 2013-509160 A | 3/2013 |
| JP | 2013-511962 A | 4/2013 |
| JP | 2015-503916 A | 2/2015 |
| JP | 2015-504667 A | 2/2015 |
| JP | 2015-506170 A | 3/2015 |
| JP | 5963375 B2 | 8/2016 |
| JP | 2016-534730 A | 11/2016 |
| JP | 2018-504127 A | 2/2018 |
| KR | 10-2018-0034640 A | 4/2018 |
| TW | 201717790 A | 6/2017 |
| TW | 201742555 A | 12/2017 |
| WO | WO 95/27412 A1 | 10/1995 |
| WO | WO 2011/050964 A1 | 5/2011 |
| WO | WO 2011/063970 A1 | 6/2011 |
| WO | WO 2013/098395 A1 | 7/2013 |
| WO | WO 2013/098409 A1 | 7/2013 |
| WO | WO 2015/062983 A2 | 5/2015 |
| WO | WO 2016/120344 A2 | 8/2016 |
| WO | WO 2017/194763 A2 | 11/2017 |
| WO | WO 2017/194769 A1 | 11/2017 |
| WO | WO 2018/002083 A1 | 1/2018 |
| WO | WO 2018/019786 A1 | 2/2018 |
| WO | WO 2016/150922 A2 | 9/2018 |
| WO | WO 2016/207407 A1 | 12/2018 |
| WO | WO 2019/208536 A1 | 10/2019 |

OTHER PUBLICATIONS

Extended European Search Report for corresponding European Application No. 19792310.5, dated Feb. 10, 2022.
International Search Report, issued in PCT/JP2019/017130, dated Jul. 16, 2019.
Japanese Office Action for Japanese Application No. 2020-515467, dated Apr. 12, 2021, with English translation.
Japanese Office Action for Japanese Application No. 2021-192706, dated Dec. 14, 2021, with an English translation.
Japanese Office Action for Japanese Application No. 2022-162899, dated Oct. 24, 2022, with an English translation.
Japanese Office Action for Japanese Application No. 2023-025234, dated Mar. 8, 2023, with an English translation.
Taiwanese Office Action and Search Report for Taiwanese Application No. 110138017 dated Oct. 26, 2022, with English Translation.
Taiwanese Office Action and Search Report for Taiwanese Application No. 110138020, dated Nov. 23, 2022, with English translation.
Korean Office Action for Korean Application No. 10-2023-7029948, dated Sep. 18, 2023, with an English translation.
Extended European Search Report for European Application No. 24189727.1, dated Dec. 10, 2024.

* cited by examiner

HEATER ASSEMBLY AND CONTAINER

CROSS REFERENCE TO RELATED APPLICATIONS

This application is a Continuation of copending application Ser. No. 18/109,110, filed on Feb. 13, 2023, now U.S. Pat. No. 11,696,601, which is a Divisional of application Ser. No. 17/078,445, filed on Oct. 23, 2020, now U.S. Pat. No. 11,805,813, which is a Continuation of PCT International Application No. PCT/JP2019/017130, filed on Apr. 23, 2019, which claims priority under 35 U.S.C. 119 (a) to Patent Application No. 2018-085336, filed in Japan on Apr. 26, 2018, all of which are hereby expressly incorporated by reference into the present application.

TECHNICAL FIELD

The invention relates to a heater assembly and a container which are intended for use in a flavor inhaler.

BACKGROUND ART

Flavor inhalers designed to heat flavor generating articles without burning have conventionally been known. The flavor inhalers each include a chamber in which a flavor generating article is contained and a heater that heats the flavor generating article contained in the chamber (for example, Patent Literatures 1 to 3).

CITATION LIST

Patent Literature

PTL 1: Japanese Unexamined Patent Application Publication (Kohyo) No. 2001-521123
PTL 2: Japanese Patent No. 5963375
PTL 3: International Publication WO 2016/207407

SUMMARY OF INVENTION

A first feature is a heater assembly comprising a container including a cylindrical portion that forms a chamber in which a flavor generating article is contained, and a heater arranged in a peripheral surface of the cylindrical portion. The container comprises a first channel extending along a longitudinal direction of the cylindrical portion and located adjacently to the chamber in a direction intersecting with the longitudinal direction of the cylindrical portion, and a second channel extending through the chamber along the longitudinal direction of the cylindrical portion. The first channel is in communication with the second channel.

In a second feature according to the first feature, the heater is so arranged as to contact an outer peripheral surface of the cylindrical portion.

In a third feature according to the first or second feature, the heater includes a heating element and a backing material that supports the heating element. The heating element is disposed along a placement area in the peripheral surface of the cylindrical portion, except an area adjacent to the first channel.

In a fourth feature according to the third feature, the placement area includes a first placement area and a second placement area in the peripheral surface of the cylindrical portion. The second placement area is located further away from the first channel than the first placement area. The heating element has higher watt density in the first placement area than in the second placement area.

In a fifth feature according to any one of the first to fourth features, the heater includes a heating element and a backing material that supports the heating element. The cylindrical portion includes a first end portion that receives the flavor generating article and a second end portion disposed on an opposite side of the cylindrical portion from the first end portion in the longitudinal direction of the cylindrical portion. The heating element is disposed away from the second end portion along the peripheral surface of the cylindrical portion.

In a sixth feature according to the fifth feature, the container includes a bottom plate portion that closes the second end portion. The heating element is disposed along the peripheral surface of the cylindrical portion without being disposed in the bottom plate portion.

In a seventh feature according to any one of the first to sixth features, the cylindrical portion includes a contact portion that comes into contact with a distal end portion of the flavor generating article when the flavor generating article is contained in the chamber.

In an eighth feature according to any one of the first to sixth features, the container includes a bottom plate portion. The container further comprises a base that is disposed in the bottom plate portion of the container and comes into contact with a distal end portion of the flavor generating article when the flavor generating article is contained in the chamber. The base forms a ring-shaped gap surrounding the base and communicated with the first channel and the second channel.

In a ninth feature according to any one of the first to eighth features, the cylindrical portion comprises a thermally conductive member.

In a 10th feature according to any one of the first to ninth features, the cylindrical portion includes a first end portion that receives the flavor generating article and a second end portion that is disposed on an opposite side of the cylindrical portion from the first end portion in the longitudinal direction of the cylindrical portion. The container includes a bottom plate portion that closes the second end portion. The cylindrical portion includes a third channel connecting the first channel and the second channel.

In an 11th feature according to the 10th feature, a channel extending from the first channel to the third channel includes an inclined channel or a curved channel.

In a 12th feature according to any one of the first to 11th features, the cylindrical portion includes a first portion that partitions the chamber and a second portion that protrudes outside the chamber in an orthogonal cross-section to the longitudinal direction of the cylindrical portion. The second portion extends along the longitudinal direction of the cylindrical portion and forms the first channel.

In a 13th feature according to the 12th feature, in a state where the flavor generating article is contained in the chamber, the first portion is in contact with an outer peripheral surface of the flavor generating article, and the second portion is away from the outer peripheral surface of the flavor generating article.

In a 14th feature according to the 12th or 13th feature, the first portion is configured to compress the flavor generating article at least partially in an arrangement direction of the first portion and the second portion when the flavor generating article is contained in the chamber.

In a 15th feature according to any one of the 12th to 14th features, the first portion has an oval circumference in a cross-section intersecting with the longitudinal direction of the cylindrical portion.

In a 16th feature according to any one of the first to 11th features, the container includes a channel forming member that forms the first channel, and the channel forming member is disposed in the outer peripheral surface of the cylindrical portion.

In a 17th feature according to the sixth feature and any one of the seventh to 16th features referring to the sixth feature, the heater assembly comprises a sensor used to detect a temperature change caused in the heater assembly, and the sensor is disposed in the bottom plate portion.

In an 18th feature according to any one of the 12th to 15th features, the heater assembly comprises a sensor used to detect a temperature change caused in the heater assembly, and the sensor is disposed in the second portion.

In a 19th feature according to the 16th feature, the heater assembly comprises a sensor used to detect a temperature change caused in the heater assembly, and the sensor is disposed in the channel forming member.

In a 20th feature according to any one of the first to 19th features, the container includes an area which is formed in at least a part of an inner peripheral surface of the cylindrical portion, the area having higher thermal emissivity than the outer peripheral surface of the cylindrical container.

In a 21st feature according to any one of the first to 20th features, the container further includes a bottom plate portion and further comprises a thermal insulating member that covers the cylindrical portion and the bottom plate portion of the container.

In a 22nd feature according to any one of the first to 21st features, the container further comprises a film that is disposed between the cylindrical portion and the heater and made of material having higher thermal conductivity than the cylindrical member.

In a 23rd feature according to any one of the first to 22nd features, the first channel forms an air channel extending from outside of the heater assembly toward the second channel and further comprises a blocking member that blocks a backward fluid flow within the first channel.

In a 24th feature according to the 23rd feature, the blocking member is a partition wall that closes a part of the first channel.

In a 25th feature according to the 23rd feature, the container further comprises a lid member that is shiftable between a first position in which the lid member exposes an opening of the container and a second position in which the lid member covers the opening, and the blocking member is the lid member that is in the first position.

A 26th feature is a container including a cylindrical portion that forms a chamber in which a flavor generating article is contained, the container comprising a first channel extending along a longitudinal direction of the cylindrical portion and located adjacently to the chamber in a direction intersecting with the longitudinal direction of the cylindrical portion, and a second channel extending through the chamber along the longitudinal direction of the cylindrical portion. The cylindrical portion includes a peripheral surface comprising a surface in which a heater is arranged. The first channel is in communication with the second channel.

DESCRIPTION OF EMBODIMENT

An embodiment will be discussion below. In the following description of the drawings, the same or similar elements are provided with the respective same or similar reference signs. However, it should be noted that the drawings are schematic diagrams and therefore that there is difference in dimensional ratio between the drawings and reality.

Specific dimensions and the like should be estimated by reference to the following discussion. Needless to say, there might be differences in dimensional relation and ratio among the drawings.

SUMMARY OF DISCLOSURE

A flavor inhaler described in BACKGROUND ART is designed with various ideas in relation to arrangement of a channel for sending air into a chamber, and a heater. However, considering that the flavor inhaler is of a small size, the arrangement of the channel and the heater needs to be further improved for efficient aerosol generation.

A heater assembly according to the summary of disclosure comprises a container including a cylindrical portion that forms a chamber containing a flavor generating article and a heater arranged in a peripheral surface of the cylindrical portion. The container comprises a first channel extending along a longitudinal direction of the cylindrical portion and located adjacently to the chamber in a direction intersecting with the longitudinal direction of the cylindrical portion and a second channel extending through the chamber along the longitudinal direction of the cylindrical portion. The first channel is in communication with the second channel.

In the summary of disclosure, the first channel communicated with the second channel extending through the chamber is located adjacently to the chamber on the premise that the heater is arranged in the peripheral surface of the cylindrical portion that forms the chamber. Such a configuration eliminates the necessity of providing a channel communicated with space under the heat assembly in the longitudinal direction of the cylindrical portion and makes it possible to employ a structure in which a bottom surface of the heater assembly is closed. It is then possible to make good use of a dead space under the heat assembly.

[Embodiment]
(Flavor Inhaler)

Figure 1:
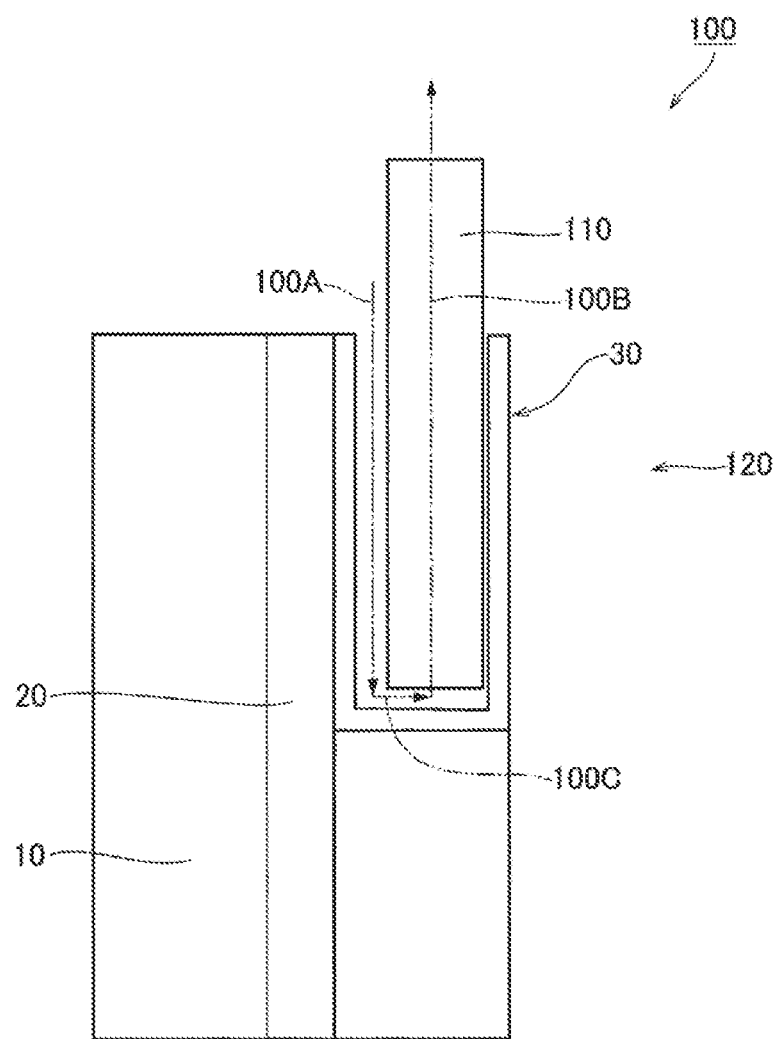
FIG. 1 shows a flavor inhaler 100 according to an embodiment.

A flavor inhaler according to an embodiment will be discussed below. FIG. 1 shows a flavor inhaler 100 according to the embodiment.

As shown in FIG. 1, the flavor inhaler 100 includes a flavor generating article 110 and an inhaler body 120. The embodiment describes as an example a case in which a user puffs the flavor generating article 110 in his/her mouth. The air inhaled by the user is guided into the user's oral cavity as an airflow 100A, an airflow 100C, and an airflow 100B in the order mentioned.

The flavor generating article 110 is backing material containing a component that can generate a flavor. The flavor generating article 110 has a shape like a pillar extending along a longitudinal direction. For example, the flavor generating article 110 may comprise shred tobacco, a compact in which tobacco material is formed into grains, a compact in which tobacco material is formed into a sheet or the like. The flavor generating article 110 may generate aerosol when heated, and in order to promote aerosol generation, may include an aerosol source containing various kinds of polyols such as glycerin, propylene glycol, and 1, 3-Butanediol. The flavor generating article 110 may comprise other plants than tobacco (for example, mint, an herb or the like). The flavor generating article 110 may contain a flavor such as menthol.

The inhaler body 120 includes a battery 10, a control circuit 20, and a heater assembly 30.

The battery 10 stores electric power used in the inhaler body 120. For example, the battery 10 is a lithium-ion battery. The battery 10 may be chargeable by an external power source.

The control circuit 20 is made up of a CPU, a memory, and the like, and controls behavior of the inhaler body 120. For example, the control circuit 20 starts heating the flavor generating article 110 in response to the user's operation of an input device, such as a push button and a slide switch, neither shown, and stops heating the flavor generating article 110 after an elapse of a predetermined period of time. If the number of puffing actions by the user exceeds a predetermined value, the control circuit 20 may stop heating the flavor generating article 110 even if the predetermined period of time does not yet elapse after the flavor generating article 110 starts being heated. For example, the puffing action is detected by a sensor 60 shown in FIG. 2 mentioned later.

The control circuit 20 may instead start heating the flavor generating article 110 in response to the start of the puffing action and stop heating the flavor generating article 110 in response to the end of the puffing action. When the predetermined period of time elapses after the puffing action is started, the control circuit 20 may stop heating the flavor generating article 110 even if the puffing action is not yet ended. According to the embodiment, the control circuit 20 is arranged between the battery 10 and the heat assembly 30 and represses thermal transmission from the heater assembly 30 to the battery 10.

Figure 2:
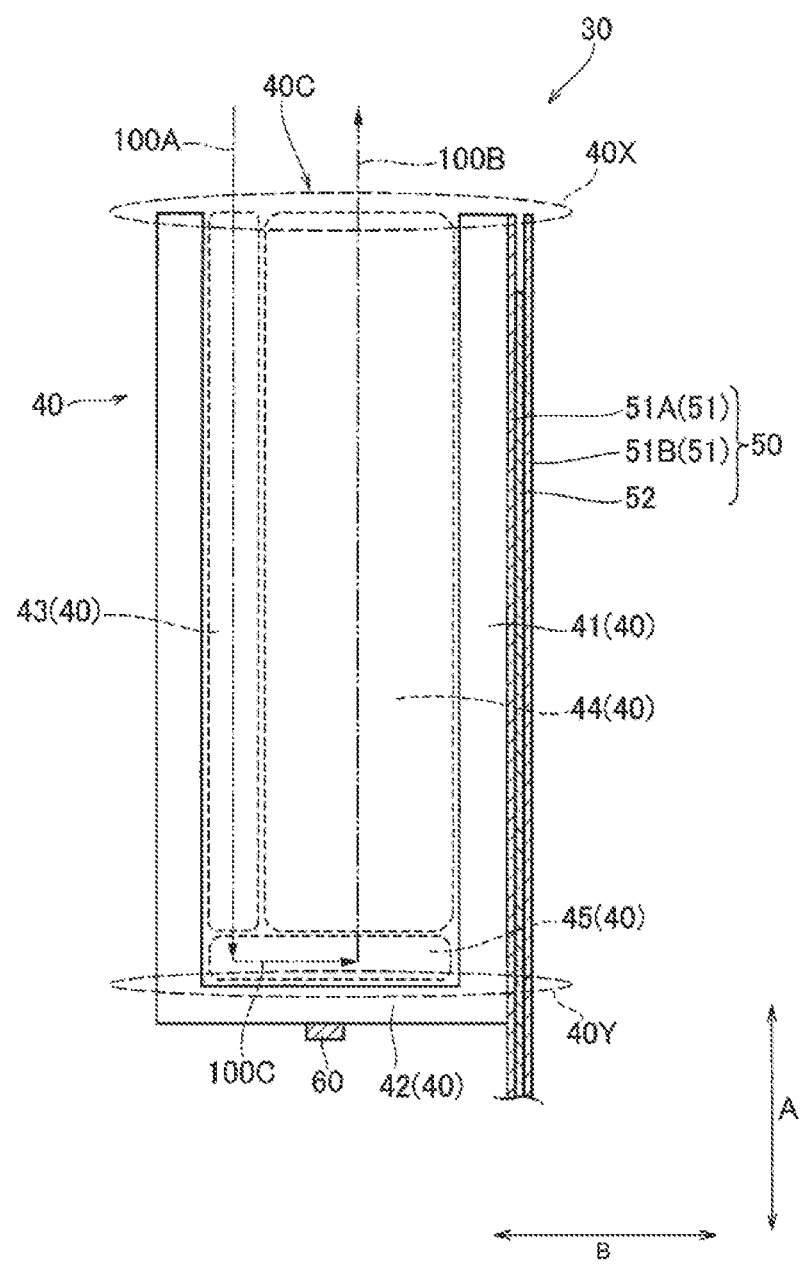
FIG. 2 shows a heater assembly 30 according to the embodiment.

The heater assembly 30 is an assembly that heats the flavor generating article 10. As shown in FIG. 2, the heater assembly 10 includes a container 40, a heater 50, and a sensor 60.

The container 40 includes a cylindrical portion 41 and a bottom plate portion 42. The cylindrical portion 41 forms a chamber 40C containing the flavor generating article 10. The cylindrical portion 41 comprises a thermally conductive member. The thermally conductive member may be but not particularly limited to aluminum or stainless (SUS), for example. The cylindrical portion 41 includes a first end portion 40X that receives the flavor generating article 10 and a second end portion 40Y that is disposed on an opposite side of the cylindrical portion 41 from the first end portion 40X in a longitudinal direction of the cylindrical portion 41 (hereinafter, referred to as a longitudinal direction A). The bottom plate portion 42 closes the second end portion 40Y. In short, the container 40 has a shape like a cup formed of the cylindrical portion 41 and the bottom plate portion 42. The container 40 may be integrally formed by a method such as metal sheet drawing.

The container 40 includes a first channel 43, a second channel 44, and a third channel 45. The first channel 43 is a channel for the airflow 100A. The first channel 43 extends along the longitudinal direction A. The first channel 43 is located adjacently to the chamber 40C in a direction intersecting with the longitudinal direction A (hereinafter, referred to as an intersecting direction B). The second channel 44 is a channel for the airflow 100B. The second channel 44 extends along the longitudinal direction A. The second channel 44 extends through the chamber 40C. The third channel 45 is a channel for the airflow 100C. The third channel 45 is disposed on the bottom plate portion 42 side and extends along the intersecting direction B. The first channel 43 is in communication with the second channel 44 through the third channel 45.

The chamber 40C is a cavity in which the flavor generating article 10 is contained and can be regarded as a portion occupied by the flavor generating article 10. As mentioned above, the second channel 44 is a channel extending through the chamber 40C and can be regarded as a channel extending through the flavor generating article 10. The second channel 44 can be regarded as synonymous with the chamber 40C and or as a part of the chamber 40C.

The heater 50 is arranged in a peripheral surface of the cylindrical portion 41 and heats the flavor generating article contained in the chamber 40C. The heater 50 may be arranged in an outer peripheral surface of the cylindrical portion 41 or may be arranged in an inner peripheral surface of the cylindrical portion 41. The heater 50 may be in contact with the peripheral surface of the cylindrical portion 41. FIG. 2 shows as an example a case in which the heater 50 is arranged in the outer peripheral surface of the cylindrical portion 41.

The heater 50 includes backing material 51 (backing material 51A and backing material 51B) and a heating element 52. The heating element is sandwiched between the backing material 51A and the backing material 51B. The backing material 51 supports the heating element. For example, the backing material 51 comprises a film such as polyimide. For example, the heating element 52 comprises a resistance heating element, such as metal. For example, the metal making up the heating element 52 may comprise one or more metals selected from nickel alloy, chromium alloy, stainless, and platinum rhodium. The heater 50 may be bonded to the peripheral surface of the cylindrical portion 41 or may be supported against the peripheral surface of the cylindrical portion 41 by a separate supporting member. Referring to FIG. 2, a thermal contraction tube, not shown, may be placed at the outside of the heater 50 so as to fix the heater 50 to the outer peripheral surface of the cylindrical portion 41 through the thermal contraction tube.

The sensor 60 is used to detect a temperature change caused in the heater assembly 30. For example, the sensor 60 is a temperature sensor, such as a thermistor and a thermocouple. The sensor 60 may be disposed in the bottom plate portion 42. The sensor may instead be disposed adjacently to the first channel 43 in an inner or outer surface of a second portion 41B described later. The sensor 60 may be used to detect the puffing action from a temperature change caused by the air flowing through the first channel 43. The sensor 60 further may be used in heating control of the flavor generating article 10 by the control circuit 20. Particularly, the control circuit 20 may be configured to discontinue power supply to the heating element 52 when temperature of the heating assembly 30 or another portion located in the inhaler 120 which is measured directly or indirectly by the sensor 60 exceeds a predetermined value.

(Container)

Figure 3:
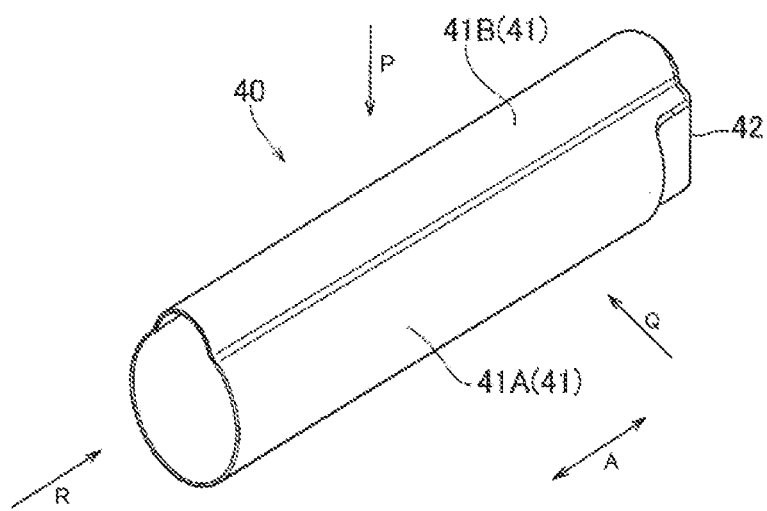
FIG. 3 shows a container 40 according to the embodiment.
Figure 4:
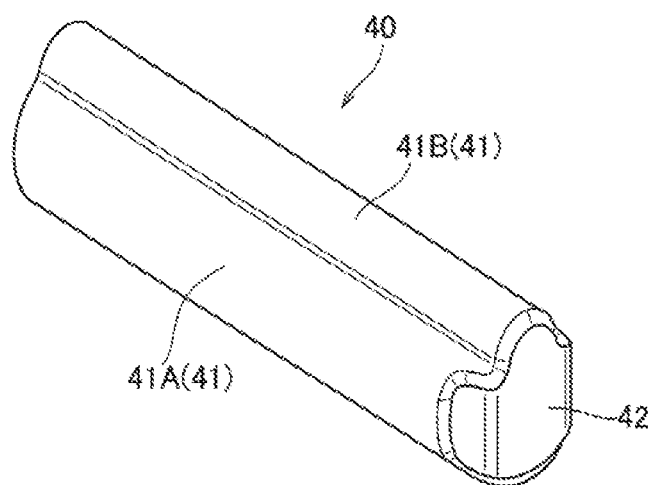
FIG. 4 shows the container 40 according to the embodiment.
Figure 5:
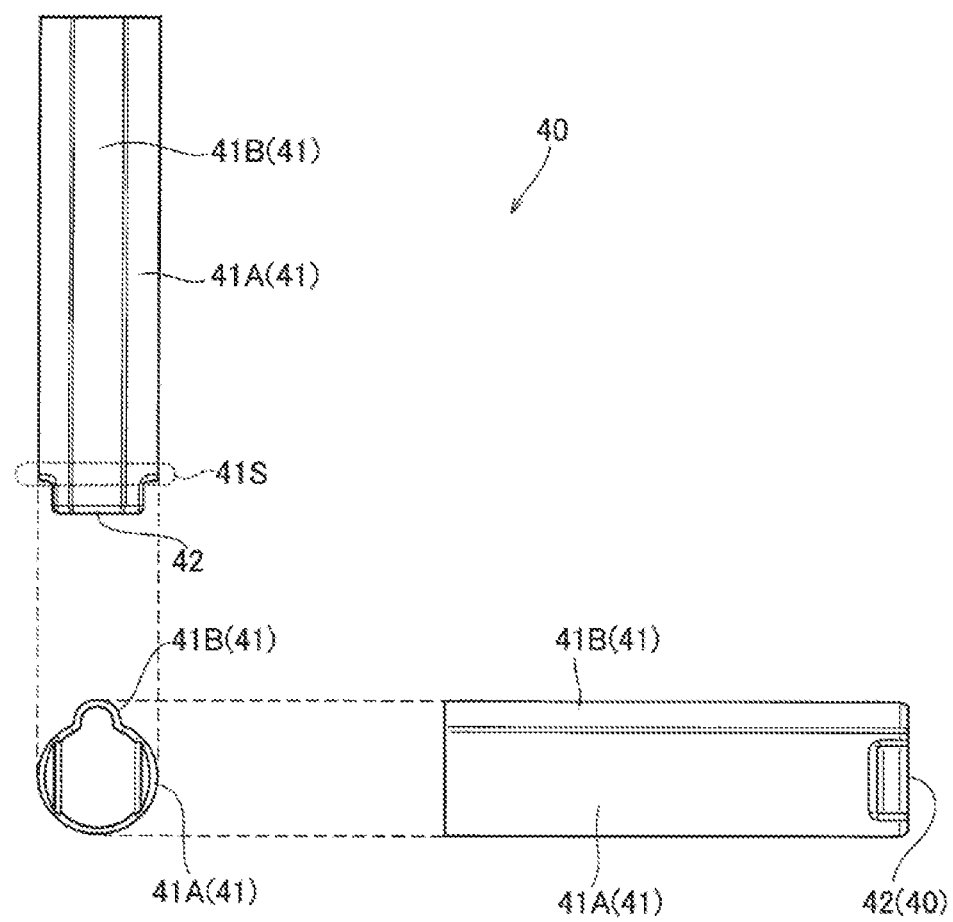
FIG. 5 shows the container 40 according to the embodiment.

The container according to the embodiment will be discussed below. FIGS. 3 and 4 are perspective views of the container 40 according to the embodiment. FIG. 5 shows the container 40 according to the embodiment as viewed from P, Q, and R directions shown in FIG. 3.

As shown in FIGS. 3 to 5, the cylindrical portion 41 of the container 40 includes a first portion 41A that partitions the chamber 40C and the second portion 41B that protrudes outside the chamber 40C in an orthogonal cross-section to the longitudinal direction A. The second portion 41B extends along the longitudinal direction A and forms the first channel 43. In other words, in a state where the flavor generating article 110 is contained in the chamber the first portion 41A is in contact with an outer peripheral surface of the flavor generating article 110, and the second portion 41B is away from the outer peripheral surface of the flavor generating article 110. The first portion 41A and the second portion 41B may be an integrally formed object.

The first portion 41A may have substantially the same shape as the flavor generating article 110 in the orthogonal cross-section to the longitudinal direction A. For example, if the flavor generating article 110 has a column-like shape, the first portion 41A may have a substantially cylindrical shape. The second portion 41B may protrude outside the chamber and has, for example, an arc-like shape in the orthogonal cross-section to the longitudinal direction A.

As shown in FIG. 5, the container 40 includes a constricted portion 41S. The constricted portion 41S forms a contact portion that comes into contact with the flavor generating article 110 when the flavor generating article 110 is contained in the chamber 40C. The constricted portion 41S may be a portion of the cylindrical portion 41 which is constricted inward without changing thickness of the cylindrical portion 41.

(Heater)

Figure 6:
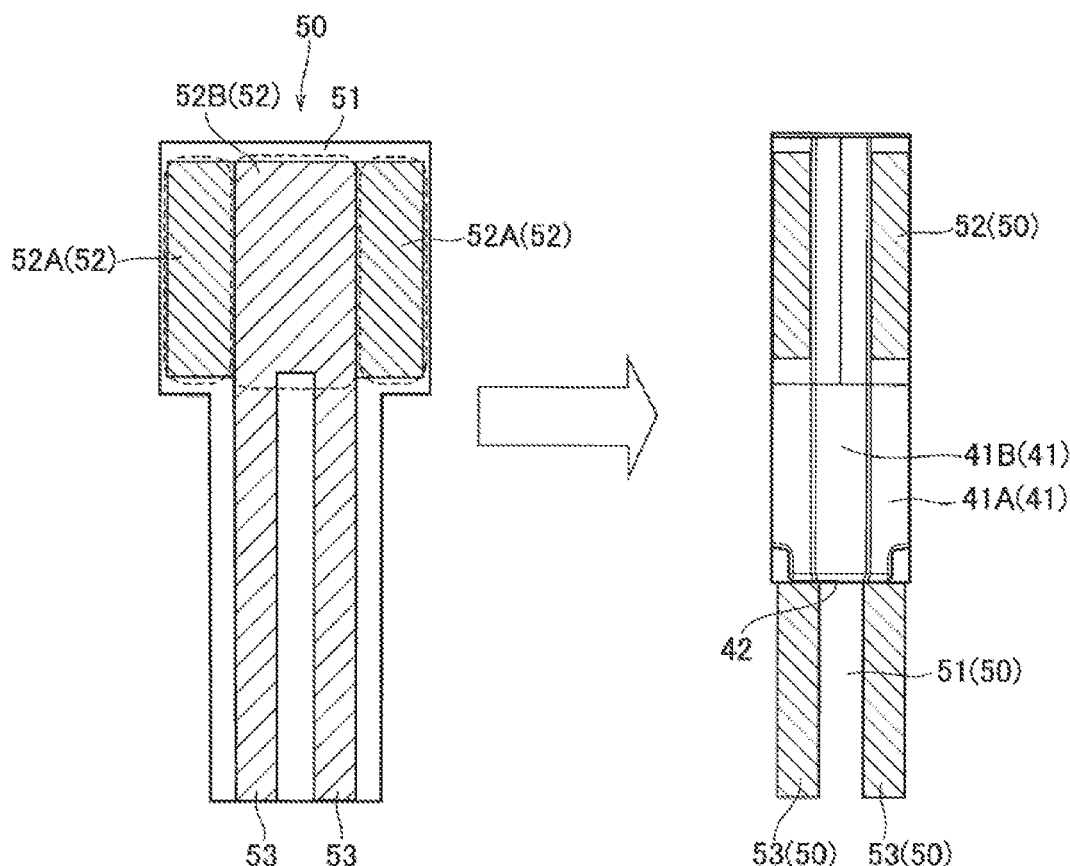
FIG. 6 is a diagram for explaining a heater 50 according to the embodiment.
Figure 7:
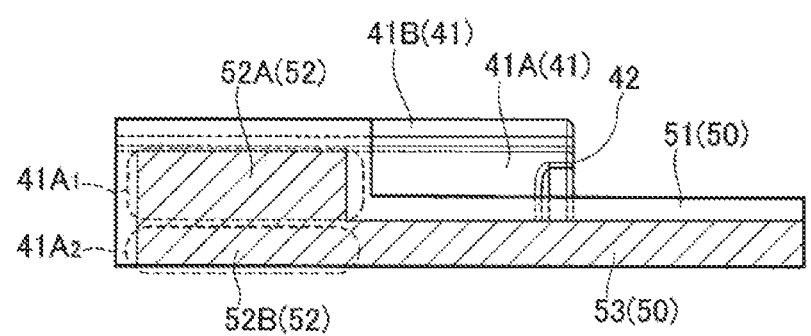
FIG. 7 is a diagram for explaining the heater 50 according to the embodiment.

The heater according to the embodiment will be discussed below. FIGS. 6 and 7 are explanatory views of the heater 50 according to the embodiment. As mentioned above, the heater 50 includes the backing material 51 and the heating element 52.

As shown in FIG. 6, the heater 50 includes a lead wire portion 53 that continues into the heating element 52. For example, the lead wire portion 53 is connected to the battery 10 through the control circuit 20.

As shown in FIGS. 6 and 7, the heater 50 is wound around the cylindrical portion 41 of the container 40. The heating element 52 is disposed along a placement area in the peripheral surface of the cylindrical portion 41, except an area adjacent to the first channel 43. According to the embodiment, the heating element 52 is disposed not along a peripheral surface of the second portion 41B but along a peripheral surface of the first portion 41A. In short, the peripheral surface of the first portion 41A forms the placement area. The backing material 51 (backing material 51A and backing material 51B) may be disposed along a part of or the entire peripheral surface of the second portion 41B or does not have to be disposed along the peripheral surface of the second portion 41B. The embodiment does not necessarily have to be thus configured. The heating element 52 may be disposed along the peripheral surfaces of both the first and second portions 41A and 41B.

The peripheral surface of the first portion 41A includes a first placement area $41A_1$ and a second placement area $41A_2$ that is located further away from the first channel 43 than the first placement area $41A_1$. A heating element 52A in the first placement area $41A_1$ may be higher in watt density than in a heating element 52B in the second placement area $41A_2$.

As shown in FIGS. 6 and 7, the heating element 52 is disposed along the peripheral surface of the cylindrical portion 41 so as to be away from the second end portion 40Y. The heating element 52 is disposed along the peripheral surface of the cylindrical portion 41 without being disposed in the bottom plate portion 42.

(Operation and Advantageous Effects)

According to the embodiment, the first channel 43 communicated with the second channel 44 extending through the chamber 40C is located adjacently to the chamber 40C on the premise that the heater 50 is arranged in the peripheral surface of the cylindrical portion 41 that forms the chamber 40C. Such a configuration eliminates the necessity of providing a channel communicated with space under the heat assembly 30 in the longitudinal direction A and makes it possible to employ a structure in which the bottom surface of the heater assembly 30 is closed. It is then possible to make good use of a dead space under the heat assembly 30. In addition, the air flowing through the first channel 43 can be preliminarily heated by the heater 50 arranged in the peripheral surface of the cylindrical portion 41, which represses a temperature decrease of the flavor generating article 110 contained in the chamber 40C and also provides an advantageous effect of efficiently generating aerosol from the flavor generating article 110.

According to the embodiment, the heater 50 is arranged in the outer peripheral surface of the cylindrical portion 41. This facilitates the assembly of the heater 50.

According to the embodiment, the heating element 52 is disposed in the placement area (peripheral surface of the first portion 41A) in the peripheral surface of the cylindrical portion 41 except a portion adjacent to the first channel 43. Such a configuration represses excessive heating of the air (airflow 100A) flowing through the first channel 43. Since the heating element 52 is not arranged in a portion that does not contribute to the heating of the flavor generating article 110 in view of the fact that the flavor generating article 110 cannot be directly heated in the portion adjacent to the first channel 43, the energy required to heat the flavor generating article 110 is saved.

According to the embodiment, the heating element 52A in the first placement area $41A_1$ may be higher in watt density than the heating element 52B in the second placement area $41A_2$. Such a configuration makes it possible to repress a temperature decrease of the flavor generating article 110 at a position adjacent to the first channel 43 in view of the fact that the heating element 52 is not arranged in the portion adjacent to the first channel 43.

According to the embodiment, the container 40 includes the constricted portion 41S that comes into contact with the flavor generating article 110 when the flavor generating article 110 is contained in the chamber 40C. Such a configuration facilitates the positioning of the flavor generating article 110 within the chamber 40C and makes it easy to secure the third channel 45 connecting the first channel 43 and the second channel 44.

According to the embodiment, the container 40 includes the bottom plate portion 42 that closes the second end portion 40Y of the cylindrical portion 41. The third channel 45 is disposed on the bottom plate portion 42 side. Such a configuration makes it possible to generate the airflow (airflow 100C) from the first channel 43 to the second channel 44 using the bottom plate portion 42.

According to the embodiment, the cylindrical portion 41 of the container 40 includes the first portion 41A that partitions the chamber 40C and the second portion 41B that protrudes outside the chamber 40C in the orthogonal cross-section to the longitudinal direction A. Such a configuration makes it possible to form an air inlet, the first channel 43, and the second channel 44 (chamber 40C) out of a single member (cylindrical portion 41), which simplifies the structure of the heater assembly 30.

According to the embodiment, since the first channel 43 is arranged adjacently to the chamber 40C, it is unnecessary to provide a channel communicated with space under the heat assembly 30 in the longitudinal direction A and makes it possible to employ the structure in which the bottom surface of the heater assembly 30 is closed. It is then possible to use the space under the heat assembly 30 for another purpose than a channel.

According to the embodiment, the sensor 60 is disposed in the bottom plate portion 42. In such a configuration, since the bottom plate portion 42 is away from the heating element 52, the sensor 60 is not overly affected by the heat generated by the heating element 52. Furthermore, since the bottom plate portion 42 is away from the user's oral cavity, the sensor 60 is not overly affected by outside air. This makes it possible to improve the sensor in accuracy for detecting temperature changes in a case where the sensor 60 is used for detection of the puffing action.

Modification Example 1

A modification example 1 of the embodiment will be now discussed. The discussion relates mainly to differences from the embodiment.

Figure 8:
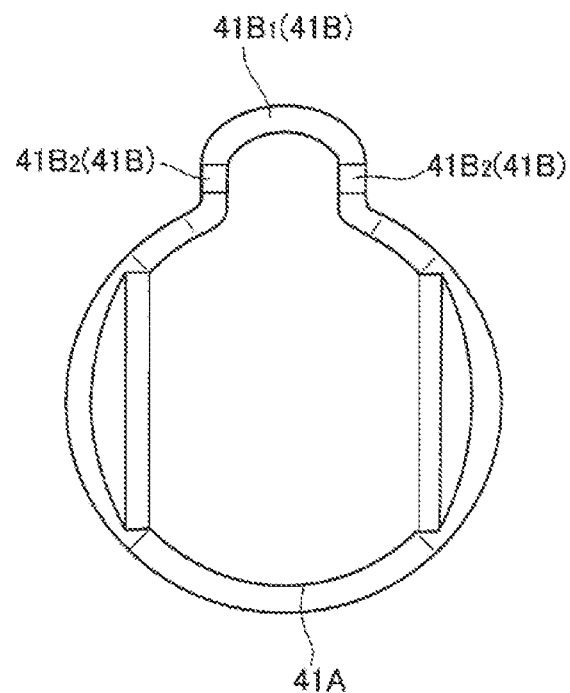
FIG. 8 is a diagram for explaining a container 40 according to a modification example 1.

According to the embodiment, the second portion 41B has an arc-like shape in the cross-section orthogonal to the longitudinal direction A. According to the modification example 1, the second portion 41B has a shape like letter U in the cross-section orthogonal to the longitudinal direction A which opens toward the chamber 40C as shown in FIG. 8. More specifically, the second portion 41B includes an arc-like portion $41B_1$ and a pair of straight portions $41B_2$. Like the examples shown in FIGS. 5 to 7, the heating element 52 of the heater 50 is disposed not along the peripheral surface of the second portion 41B but along the peripheral surface of the first portion 41A. The backing material 51 (backing material 51A and backing material 51B) of the heater 50 may be disposed along the pair of straight portions $41B_2$ of the second portion 41B and further may be disposed along the arc-like portion $41B_1$.

The embodiment and the modification example 1 do not necessarily have to be configured as described above. The second portion 41B may be designed in any way as long as it protrudes outside the chamber 40C in the orthogonal cross-section to the longitudinal direction A. The second portion 41B may have a rectangular shape or may have a shape of combination of a rectangle and an arc.

Modification Example 2

The following discussion explains a modification example 2 of the embodiment. The discussion relates mainly to differences from the embodiment.

The modification example 2 relates to a variation of the shape of the cylindrical portion 41. In the modification example 2 as well as in the embodiment, the cylindrical portion 41 includes the first portion 41A that partitions the chamber 40C and the second portion 41B that protrudes outside the chamber 40C in the orthogonal cross-section to the longitudinal direction A.

Figure 9:
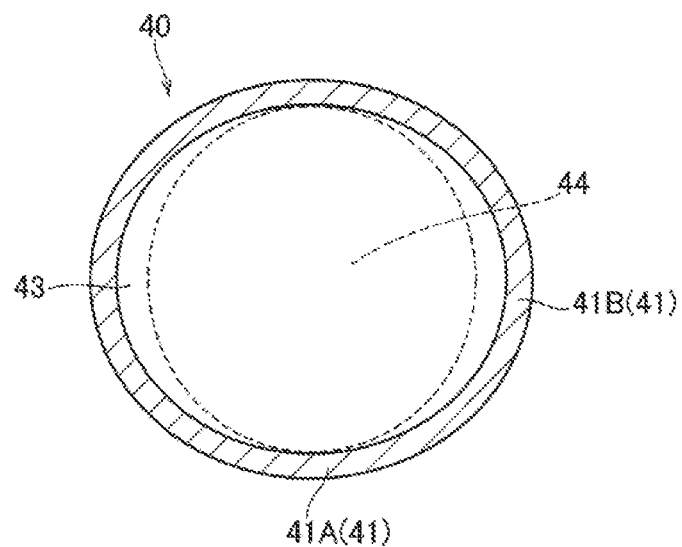
FIG. 9 is a diagram for explaining a container 40 according to a modification example 2.

For example, when the flavor generating article 110 has a circular cross-section as shown in FIG. 9, the cylindrical portion 41 may have an oval shape in the cross-section orthogonal to the longitudinal direction A. In such a case, the first channel 43 is formed between the inner peripheral surface of the cylindrical portion 41 and the outer peripheral surface of the flavor generating article 110. A portion in the cylindrical portion 41 which is in contact with the outer peripheral surface of the flavor generating article 110 forms the first portion 41A, and a portion in the cylindrical portion 41 which is away from the outer peripheral surface of the flavor generating article 110 forms the second portion 41B.

Figure 10:
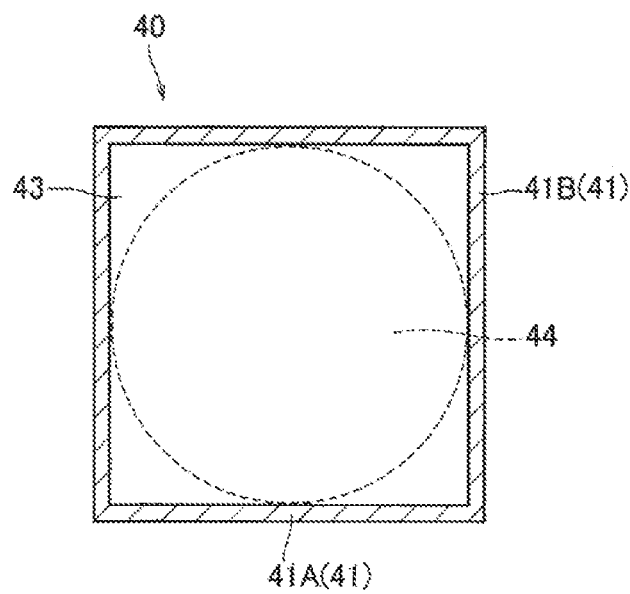
FIG. 10 is a diagram for explaining the container 40 according to the modification example 2.

For example, when the flavor generating article 110 has a circular cross-section as shown in FIG. 10, the cylindrical portion 41 may have a rectangular shape in the cross-section orthogonal to the longitudinal direction A. In such a case, the first channel 43 is formed between the inner peripheral surface of the cylindrical portion 41 and the outer peripheral surface of the flavor generating article 110. A portion in the cylindrical portion 41 which is in contact with the outer peripheral surface of the flavor generating article 110 forms the first portion 41A, and a portion in the cylindrical portion 41 which is away from the outer peripheral surface of the flavor generating article 110 forms the second portion 41B.

Modification Example 3

A modification example 3 of the embodiment will be discussed below. The discussion relates mainly to differences from the embodiment.

In the modification example 3, the container 40 includes a channel forming member that forms the first channel 43. The channel forming member is disposed in the outer peripheral surface of the cylindrical portion 41.

Figure 11:
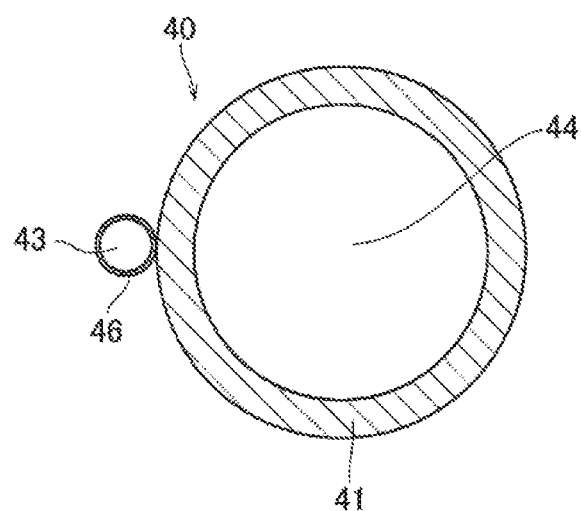
FIG. 11 is a diagram for explaining a container 40 according to a modification example 3.

For example, the container 40 may include a channel forming member 46 having a circular shape in a cross-section orthogonal to the longitudinal direction A as shown in FIG. 11. In other words, the channel forming member 46 may have a shape like a circular cylinder extending along the longitudinal direction A. In such a case, the first channel 43 is formed on an inner side of the channel forming member 46. The channel forming member 46 may be bonded to the outer peripheral surface of the cylindrical portion 41 or formed integrally with the cylindrical portion 41.

Figure 12:
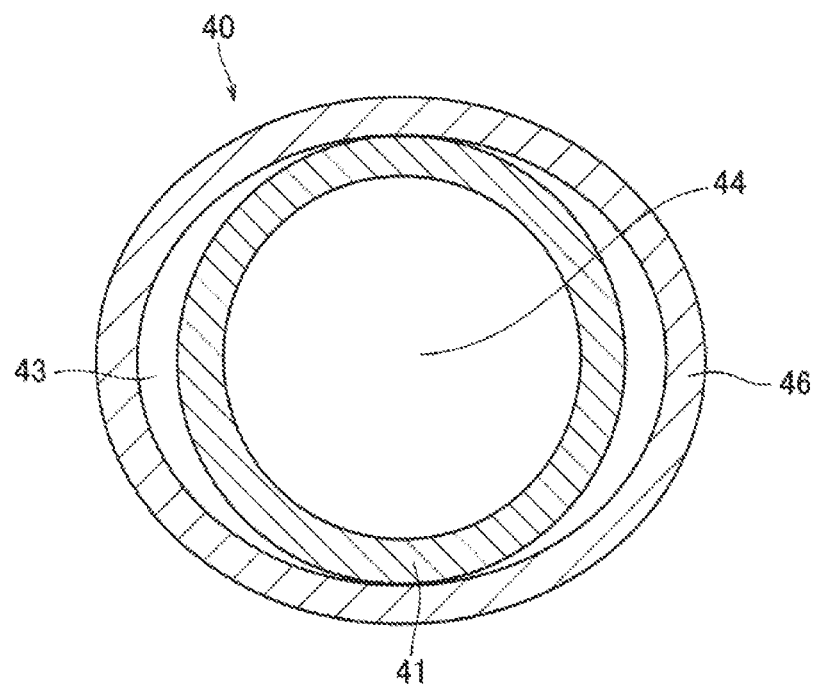
FIG. 12 is a diagram for explaining the container 40 according to the modification example 3.

For example, the container 40 may include the channel forming member 46 which contains the cylindrical portion 41 and has an oval shape in the cross-section orthogonal to the longitudinal direction A as shown in FIG. 12. In other words, the channel forming member 46 may have a shape like an oval cylinder extending along the longitudinal direction A. In such a case, the first channel 43 is formed between an inner peripheral surface of the channel forming member 46 and the outer peripheral surface of the cylindrical portion 41. The channel forming member 46 may be bonded to the outer peripheral surface of the cylindrical portion 41 or formed integrally with the cylindrical portion 41.
(Operation and Advantageous Effects)

According to the modification example 3, the container 40 includes the channel forming member 46 that forms the first channel 43. Such a configuration represses an unintended inflow of air from the first channel 43 to the second channel 44 since the first channel 43 and the second channel 44 (chamber 40C) are separated at least by the cylindrical portion 41. The unintended inflow of air is an inflow of air passing through other channels than the third channel 45.

In the example shown in FIG. 12, the heater 50 arranged in the peripheral surface of the cylindrical portion 41 is arranged further inside than the first channel 43. In other words, since the first channel 43 is not interposed between the heater 50 and the chamber 40C, energy is efficiently transmitted from the heater 50 to the flavor generating article 110 as compared to the case shown in FIG. 9.]]

Modification Example 4

A modification example 4 of the embodiment will be discussed below. The discussion relates mainly to differences from the embodiment.

The modification example 4 relates to a variation of the contact portion that comes into contact with the flavor generating article 110 when the flavor generating article 110 is contained in the chamber 40C.

Figure 13:
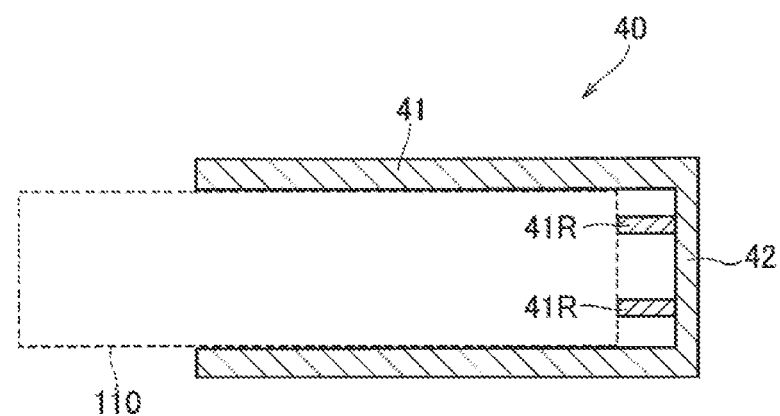
FIG. 13 is a diagram for explaining a contact portion according to a modification example 4.

For example, the container 40 includes ribs 41R disposed in the bottom surface 42 in a standing manner as shown in FIG. 13. Although FIG. 13 shows two ribs 41R as an example, the number of the ribs 41R may be freely determined.

Figure 14:
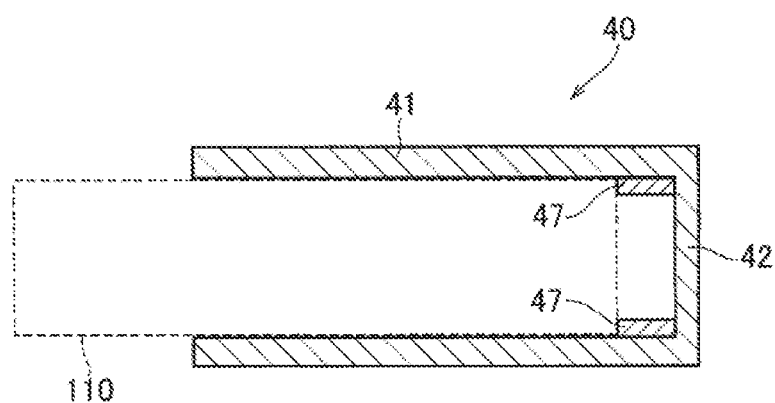
FIG. 14 is a diagram for explaining the contact portion according to the modification example 4.

For example, the container 40 may include a stepped portion 47 disposed in the inner peripheral surface of the cylindrical portion 41 as a contact portion as shown in FIG. 14. The stepped portion 47 is a portion protruding from the inner peripheral surface of the cylindrical portion 41 toward the inside of the chamber 40C. The stepped portion 47 may be either in contact with or located away from the bottom surface 42. The stepped portion 47 may be a portion continued into the entire inner peripheral surface of the cylindrical portion 41 and also may be disposed intermittently in the inner peripheral surface of the cylindrical portion 41. If the stepped portion 47 is intermittently disposed, the number of stepped portions 47 may be freely determined. In such a case, the stepped portions 47 may be formed of a heat dissipation member.

Figure 15A:
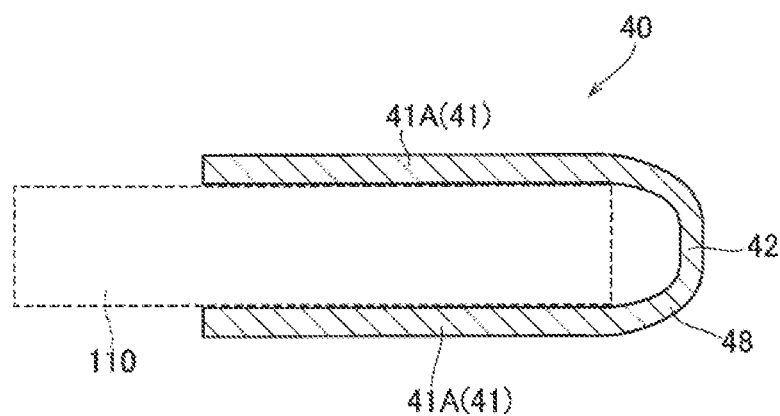
FIG. 15(A) and FIG. 15(B) are diagrams for explaining the contact portion according to the modification example 4.
Figure 15B:
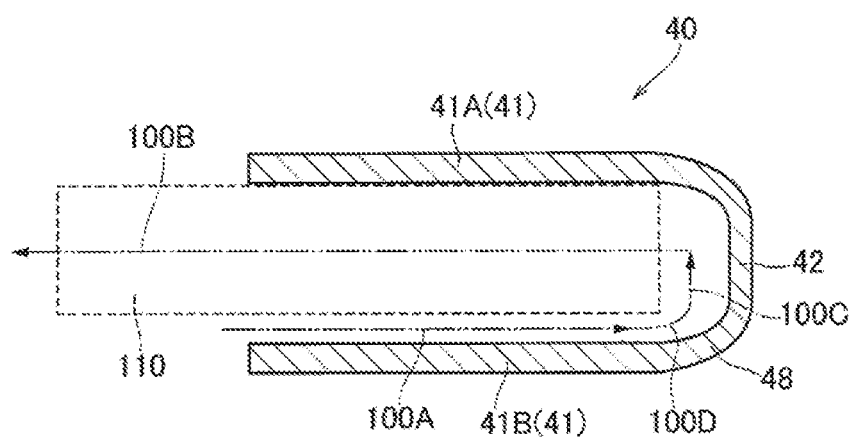

For example, as shown in FIG. 15(A), the first portion 41A partitioning the chamber 40C has an inner peripheral surface that may be tapered toward the second end portion 41Y in an orthogonal cross-section to the longitudinal direction A. In such a case, a portion in an inner peripheral surface of the first portion 41A, which contacts the flavor generating article 110, functions as a contact portion. As well as the inner peripheral surface of the first portion 41A, an inner peripheral surface of the second portion 41B also may be tapered toward the second end portion 41Y. In such a configuration, as shown in FIG. 15(B), a channel extending from the first channel 43 to the third channel 45 includes an inclined or curved channel. The inclined or curved channel may be regarded as a part of the first channel 43 or as a part of the third channel 45. An airflow 100D passing through the inclined or curved channel is generated, which allows air to flow smoothly from the first channel 43 toward the second channel 44.

Figure 16:
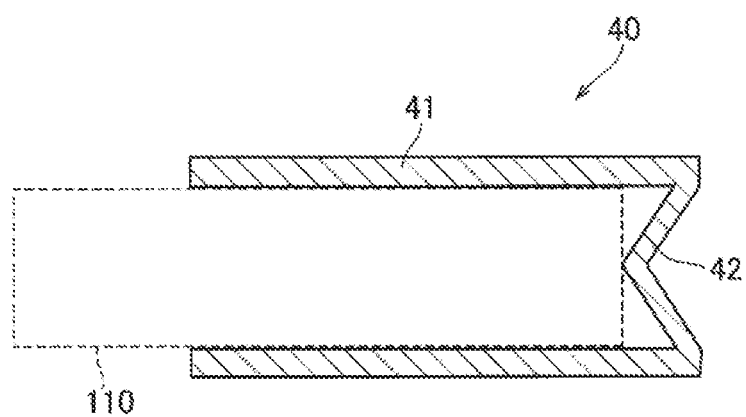
FIG. 16 is a diagram for explaining the contact portion according to the modification example 4.

For example, as shown in FIG. 16, the bottom surface 42 of the container 40 may have a shape protruding toward the inside of the chamber 40C. In such a case, a portion in the bottom surface 4, which contacts the flavor generating article 110, functions as a contact portion. Due to the above-mentioned shape, the bottom surface 42 functions similarly to the ribs 41R.

Modification Example 5

A modification example 5 of the embodiment will be discussed below. The discussion relates mainly to differences from the embodiment.

Figure 17A:
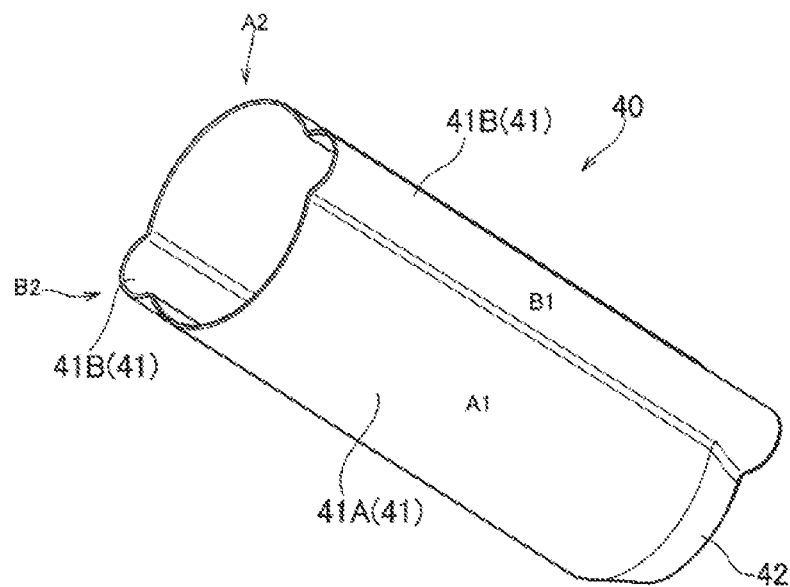
FIG. 17(A) and FIG. 17(B) are diagrams for explaining a container 40 according to a modification example 5.
Figure 17B:
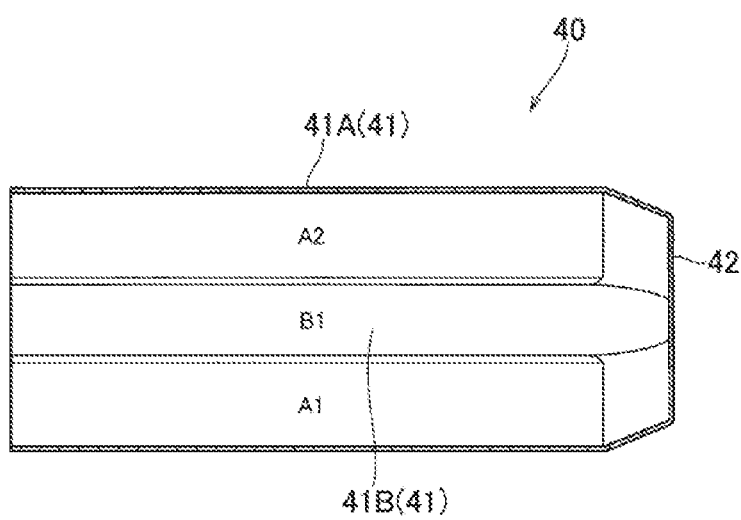
Figure 18:
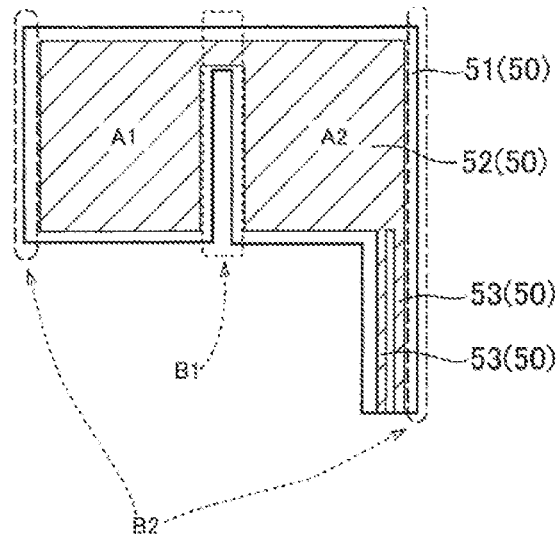
FIG. 18 is a diagram for explaining a heater 50 according to the modification example 5.
Figure 19:
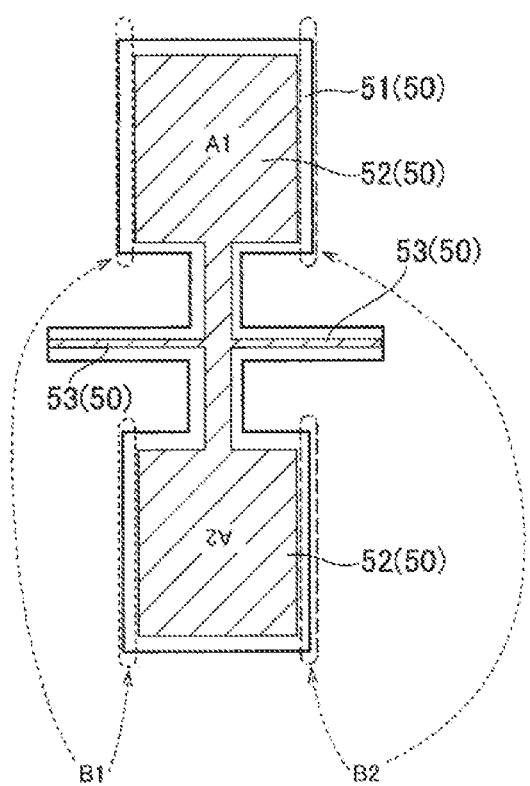
FIG. 19 is a diagram for explaining the heater 50 according to the modification example 5.
Figure 20:
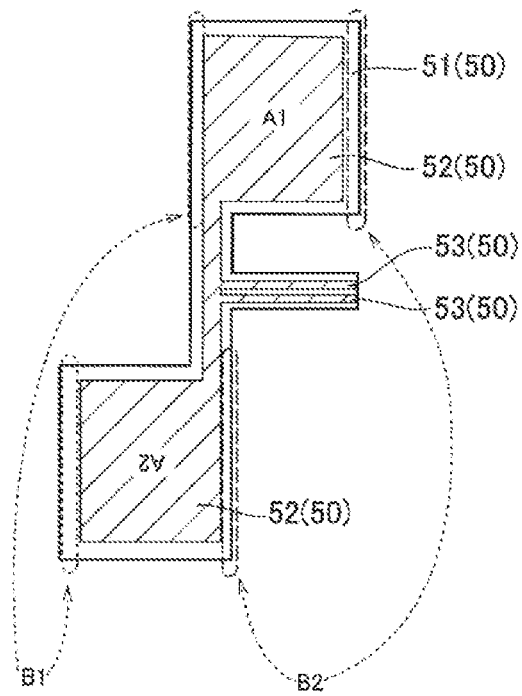
FIG. 20 is a diagram for explaining the heater 50 according to the modification example 5.

The modification example 5 relates to variation of the heater 50. As shown in FIG. 17, the modification example 5 relates to a case in which the container 40 includes two first channels 43. In FIGS. 17, A1 and A2 are reference signs representing an outer peripheral surface of the first portion 41A, and B1 and B2 are reference signs representing an outer peripheral surface of the second portion 41B. In FIGS. 18 to 20 described below, an area for the heater 50 to be disposed in the outer peripheral surface of the first portion 41A is provided with reference signs A1 and A2, and an area for the heater 50 to be disposed in the outer peripheral surface of the second portion 41B is provided with reference signs B1 and B2. That is, in the heater assembly 30 after being assembled, the areas provided with reference signs A1, A2, B1, and B2 in FIG. 18 face areas provided with the same respective reference signs in FIG. 17. This applies to examples shown in FIGS. 19 and 20.

For example, as shown in FIG. 18, a heating element 52 of the heater 50 may be divided into two heating portions. The two heating portions are disposed along the outer peripheral surface of the first portion 41A, and other portions are disposed in the outer peripheral surface of the second portion 41B. A lead wire 53 may be disposed at one end of the heater 50.

For example, as shown in FIG. 19, the heating element 52 of the heater 50 may be divided into two heating portions. The two heating portions are disposed along the outer peripheral surface of the first portion 41A, and other portions are disposed in the outer peripheral surface of the second portion 41B. A lead wire 53 may be disposed in a portion connecting the two heating portions.

For example, as shown in FIG. 20, the heating element 52 of the heater 50 does not necessarily have to be divided into two heating portions. In the heater 50, the two heating portions are disposed along the outer peripheral surface of the first portion 41A, and other portions are disposed in the outer peripheral surface of the second portion 41B. The lead wire 53 may be disposed in the portion connecting the two heating portions.

Modification Example 6

A modification example 6 of the embodiment will be discussed below. The discussion relates mainly to differences from the embodiment.

Figure 21:
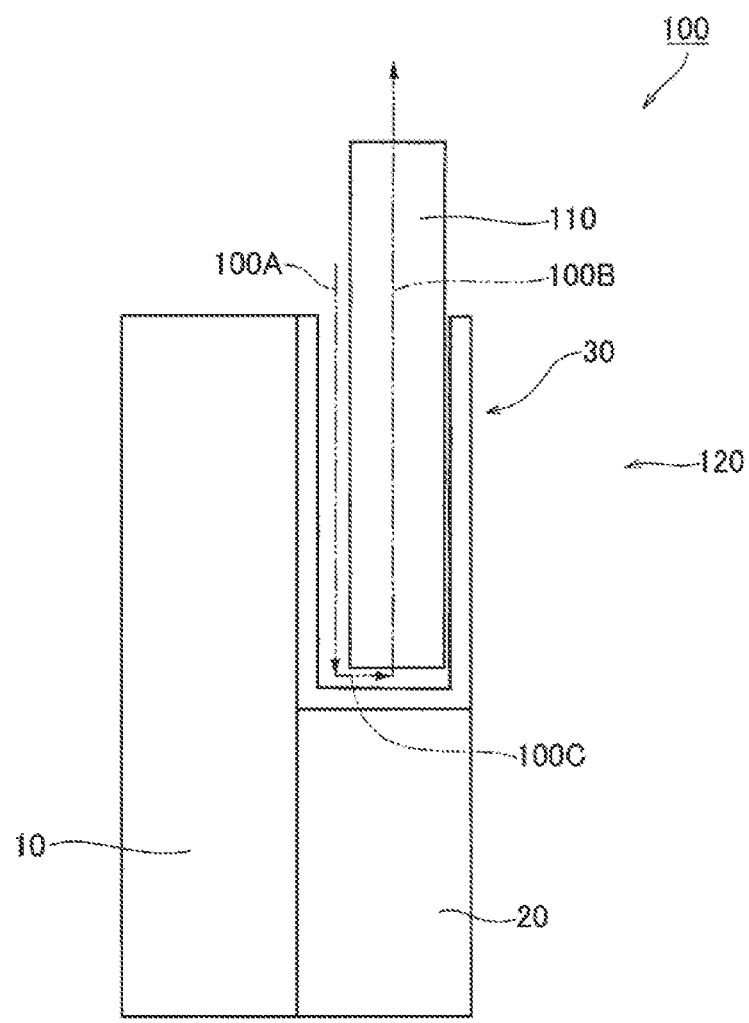
FIG. 21 shows a flavor inhaler 100 according to a modification example 6.

According to the embodiment, the control circuit 20 is arranged between the battery and the heater assembly 30. In contrast, according to the modification example 6, the control circuit 20 is disposed under the heater assembly 30 as shown in FIG. 21.

In the modification example 6, as in the embodiment, the first channel 43 is arranged adjacently to the chamber 40C. This eliminates the necessity of providing a channel communicated with the space under the heat assembly 30 in the longitudinal direction A and makes it possible to employ a structure in which the bottom surface of the heater assembly 30 is closed. It is then possible to arrange the control circuit 20 under the heater assembly 30 and make good use of the dead space under the heater assembly 30.

Other Embodiments

The invention has been discussed with reference to the embodiment. It should be noted, however, that the discussion and drawings which are part of the disclosure are not intended to limit the invention. The disclosure clearly articulates to a person with ordinary skill in the art a variety of alternative embodiments, embodiments, and operation technology.

In the embodiment, the sensor 60 is disposed in the bottom plate portion 42. In such a case, the sensor 60 may be disposed in either an inner or outer surface of the bottom plate portion 42. The embodiment, however, does not necessarily have to be configured that way. The sensor 60 may be located adjacently to the first channel 43. In such a case, the sensor 60 may be disposed in either the outer or inner peripheral surface of the second portion 41B and further may be disposed in either an outer or inner peripheral surface of the channel forming member 46. In such a configuration, the sensor 60 is located away from the heating element 52 and therefore is not overly affected by the heat generated by the heater 50. Accordingly, the sensor 60 is improved in accuracy for detecting a temperature change when the sensor 60 is used to detect a puffing action.

The discussion about the embodiment describes as an example the case in which the container 40 includes the single first channel 43. The embodiment, however, does not necessarily have to be configured that way. The container 40 may include two or more first channels 43. In such a case, the two or more first channels 43 may be arranged at regular intervals in the peripheral surface of the cylindrical portion 41.

Additional Modification Example 1

The following discussion will explain an additional modification example 1 of the embodiment. In the additional modification example 1, for example, the container 40 shown in FIG. 2 includes an area which is formed at least partially in the inner peripheral surface of the cylindrical portion 41, the area having higher thermal emissivity than the outer peripheral surface of the cylindrical container 41.

The area having high thermal emissivity may be formed by blackening the inner peripheral surface of the cylindrical member 41. Specifically, the area having high thermal emissivity may be formed by applying carbon pigment or attaching a graphite film to the inner peripheral surface of the cylindrical member 41 to provide a black layer. Although material for forming the black layer is not particularly limited, it is preferable to use material, such as carbon, ceramic, silicon, and glass, which is high both in thermal emissivity and in thermal conductivity.

The area having high thermal emissivity does not necessarily have to be formed by blackening the inner peripheral surface of the cylindrical member 41 but may be formed by causing oxidation corrosion to roughen the inner peripheral surface of the cylindrical member 41, mechanically roughening the inner peripheral surface of the cylindrical member 41 or forming an oxide film on the inner peripheral surface of the cylindrical member 41.

Consequently, the inner peripheral surface of the cylindrical portion 41 becomes higher in thermal emissivity than aluminum and stainless (SUS) from which the inner peripheral surface of the cylindrical portion 41 is made. It is then possible to intensify the heating of the flavor generating article 110 through thermal emission.

The area having high thermal emissivity may be disposed in the entire inner peripheral surface of the cylindrical member 41 or, for example, may be disposed only in the first portion 41A while avoiding the second portion 41B shown in FIG. 3.

Additional Modification Example 2

An additional modification example 2 of the embodiment will be now discussed with reference to FIG. 22. According to the additional modification example 2, for example, the first portion 41A shown in FIG. 22 may be configured to compress the flavor generating article at least partially in a direction of arrangement of the first portion 41A and the second portion 41B when the flavor generating article is contained in the container 40. Hereinafter, the direction of arrangement of the first portion 41A and the second portion 41B will be occasionally referred to simply as "arrangement direction." FIG. 23 is a top view of an opening OP of the container 40 in FIG. 22 as viewed in the longitudinal direction A. FIG. 24 is a cross-sectional view of the container 40 at a point SC in FIG. 22. The inner periphery of the first portion 41A shown in FIG. 24 may be configured to compress the flavor generating article in the arrangement direction (vertical direction in FIG. 24) when the flavor generating article is contained in the container 40. Particularly, the inner periphery of the first portion 41A shown in FIG. 24 includes a curved portion 41A3 allowed to contact an outer periphery of a smoking article and a pair of straight portions 41A5, 41A5 extending from both end portions 41A4, 41A4 of the curved portion 41A3 toward a top portion 41B3 located in a protruding direction of the second portion 41B. The curved portion 41A3 of the present example may be formed of a part of an oval with a long axis intersecting with the arrangement direction.

Figure 24:
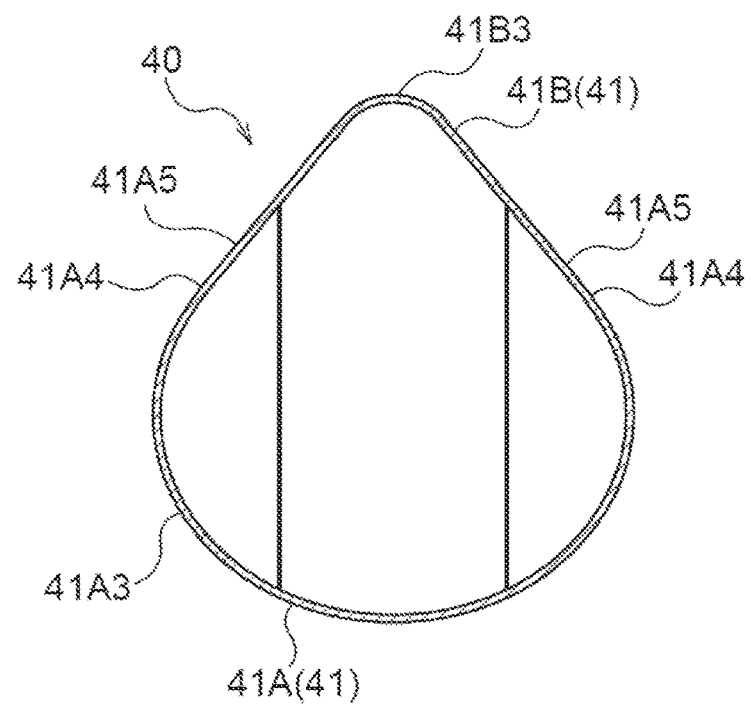
FIG. 24 is a diagram for explaining the container 40 according to the additional modification example 2.
Figure 25:
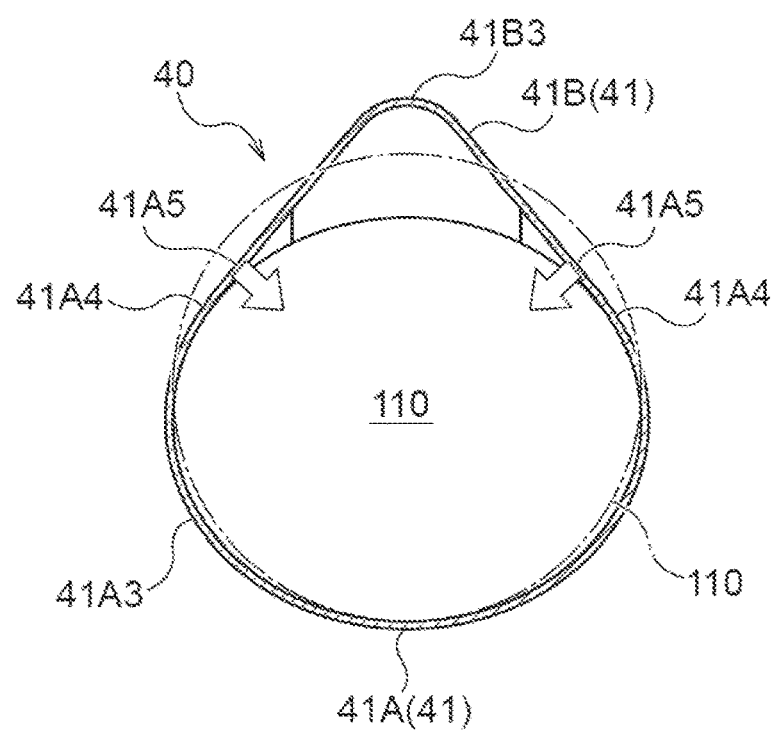
FIG. 25 is a diagram for explaining the container 40 according to the additional modification example 2.

FIG. 25 is a cross-sectional view of a substantially column-like flavor generating article 110 contained in the container 40 in FIG. 24. As shown in FIG. 25, the flavor generating article 110 is pressed in a radially inward direction (obliquely downward in the drawing) by the straight portions 41A5, 41A5 of the first portion 41A and the curved portion 41A3 located adjacently thereto. An outer surface of the flavor generating article 110 then comes into tight contact with an inner surface of the first portion 41A. The first portion 41A of the container 40 is directly heated by various heaters, so that the flavor generating article 110 is improved in heating efficiency by being brought into tight contact with the inner surface of the first portion 41A. FIG. 25 shows, for comparison, a broken line representing an outer periphery of the flavor generating article 110 in a state before being contained in the container 40 and compressed.

According to the example shown in FIG. 25, the pair of straight portions 41A5, 41A5 of the first portion 41A and the curved portion 41A3 located adjacently thereto press the outer surface of the flavor generating article 110 in a direction of an arrow in the drawing (obliquely downward), which represses the entry of the flavor generating article 110 into an internal space of the second portion 41B. When the container 40 is fitted in the flavor inhaler, the internal space of the second portion 41B can form the first channel 43 (see FIG. 2) that functions as an air channel. Therefore, the repression of entry of the flavor generating article 110 into the internal space prevents the air channel in the flavor inhaler from being increased in airflow resistance. The container 40 of the present example may have a cross-section that is capable of compressing the flavor generating article as described across the entire longitudinal length thereof or only in a part of the longitudinal length thereof. The container 40 shown in FIG. 25 has such a cross-section in a most part in the longitudinal length except upper and lower end portions thereof.

Figure 22:
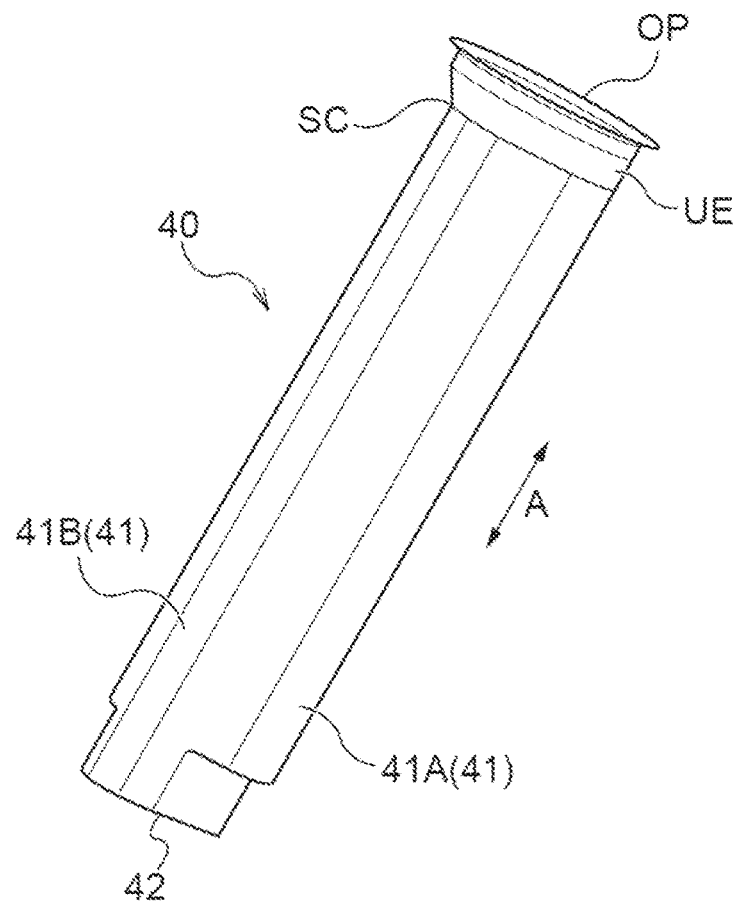
FIG. 22 is a diagram for explaining a container 40 according to an additional modification example 2.
Figure 23:
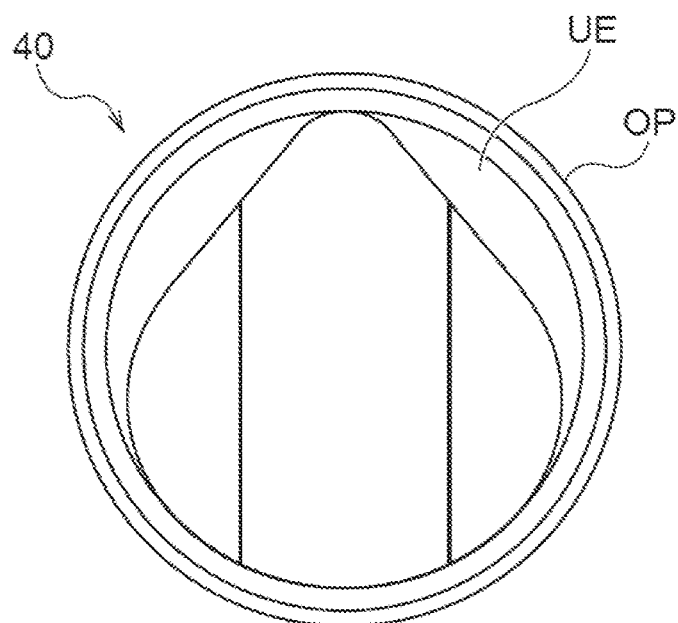
FIG. 23 is a diagram for explaining the container 40 according to the additional modification example 2.

Referring to FIGS. 22 and 23, the container 40 of the present example further includes a hollow upper edge portion UE located between the first portion 41A and the opening OP. According to the example shown in FIG. 23, the opening OP of the container 40 has an inner periphery that is substantially equal to or slightly larger than the outer periphery of the flavor generating article 110. The upper edge portion UE has an inner periphery that is tapered from the opening OP toward the first portion 41A. That is, an inner peripheral surface of the upper edge portion UE of the container 40 functions to guide the flavor generating article inserted from the opening OP toward the first portion 41A.

Figure 26:
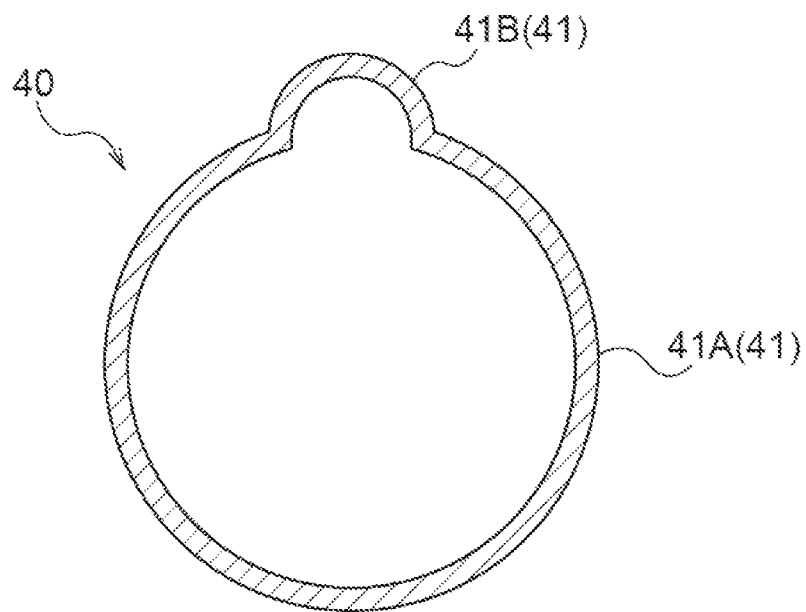
FIG. 26 is a diagram for explaining the container 40 according to the additional modification example 2.
Figure 27:
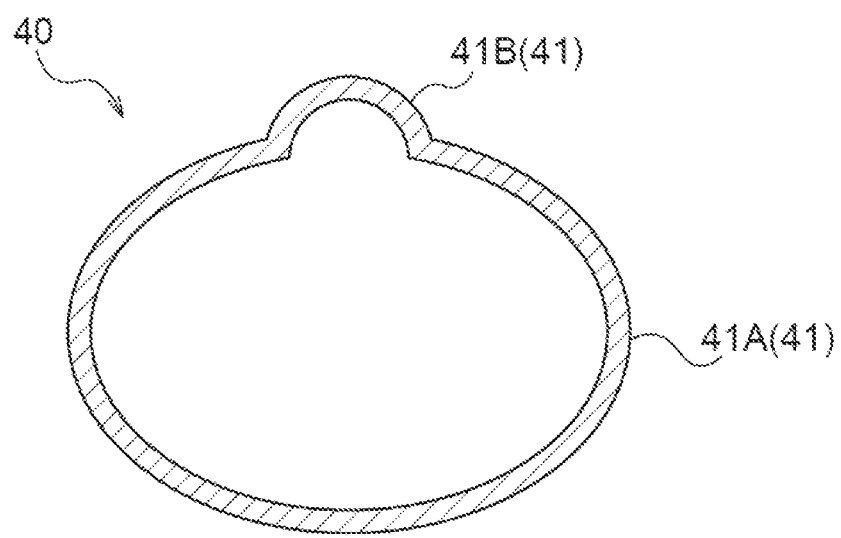
FIG. 27 is a diagram for explaining the container 40 according to the additional modification example 2.

The following discussion will explain another example of the cross-sectional shape of the container 40. For example, the first portion 41A shown in FIG. 3 may have various cross-sectional shapes at different longitudinal positions. The various cross-sectional shapes are shown in FIGS. 26 and 27 as examples. The inner periphery of the first portion 41A shown in FIG. 26 is formed of a part of a circle. The inner periphery of the first portion 41A shown in FIG. 27 is formed of a part of an oval with a long axis intersecting with the arrangement direction. Unlike the example shown in FIG. 25 described above, the inner periphery of the first portion 41A shown in FIG. 27 does not have a pair of straight portions but is capable of compressing the flavor generating article in the arrangement direction (vertical direction in FIG. 24) as with the example shown in FIG. 25. The container 40 may be so configured that the cross-sectional shape of the first portion 41A changes in a continuous manner from the shape shown in FIG. 26 to the shape shown in FIG. 27.

Area of the cross-section of the first portion 41A may be constant at any longitudinal position or may change at different longitudinal positions. For example, if the first portion 41A has the cross-sections shown in FIGS. 26 and 27 at different longitudinal positions, the first portion 41A in FIG. 27 may be set smaller in cross-sectional area than the first portion 41A in FIG. 26. The cross-sectional area of the first portion 41A here means virtual circular or oval area overlapping with the inner periphery of the first portion 41A. If the cross-section of the first portion 41A which is shaped into an oval as described is made relatively small, the flavor generating article is firmly compressed. Consequently, the outer periphery of the flavor generating article is brought into firm and tight contact with the inner periphery of the first portion 41A. In general, the flavor generating article 110 comprises a tobacco portion including tobacco material at a distal end side and a paper tube portion including a filter at a proximal end side. The tobacco portion is easily deformed by an external force, whereas the paper tube portion is hard to be deformed. It is therefore preferable that an oval inner periphery as in FIG. 27 be provided to the tobacco portion, and that a circular inner periphery as in FIG. 26 be provided to the paper tube portion.

Additional Modification Example 3

An additional modification example 3 of the embodiment will be discussed below. According to the additional modification example 3, the first channel 43 formed by the second portion 41B may form an air channel extending from outside of the heater assembly and the favor inhaler in which the heater assembly is fitted toward the second channel 44 formed by the first portion 41A (see FIGS. 2 and 3 and the like). The heater assembly and the flavor inhaler in which the heater assembly is fitted according to the present example may be provided with a blocking member that blocks a backward fluid flow within the first channel 43. For example, the container 40 of the heater assembly shown in FIG. 3 may be provided with a partition wall 49 as the blocking member which is formed in the second portion 41B and closes a part of the first channel.

Figure 28:
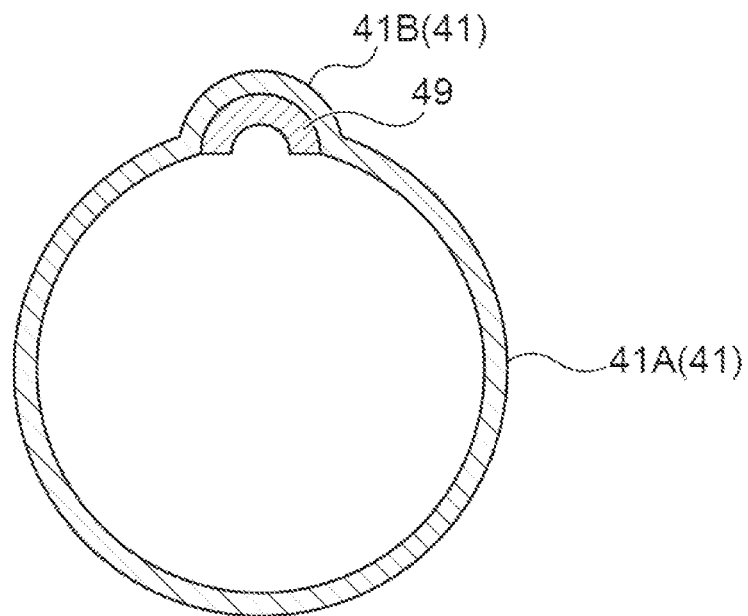
FIG. 28 is a diagram for explaining a partition wall 49 according to an additional modification example 3.
Figure 29:
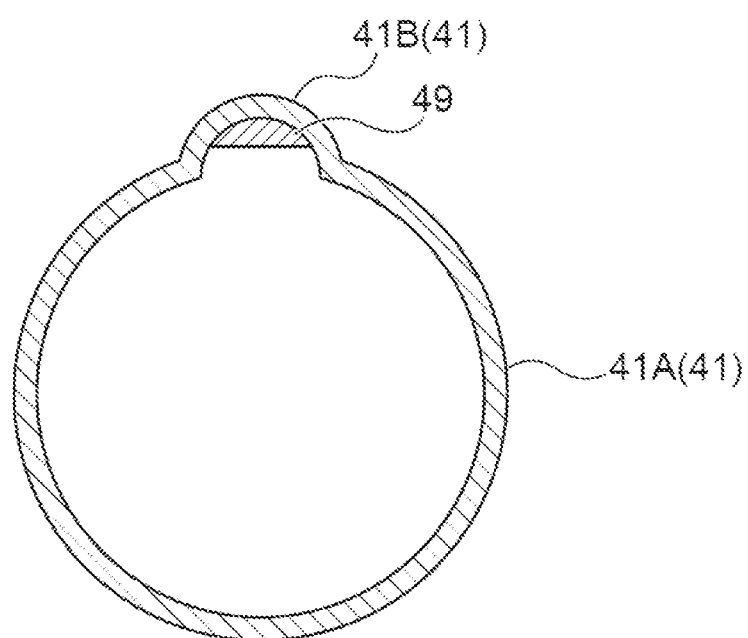
FIG. 29 is a diagram for explaining the partition wall 49 according to the additional modification example 3.
Figure 30:
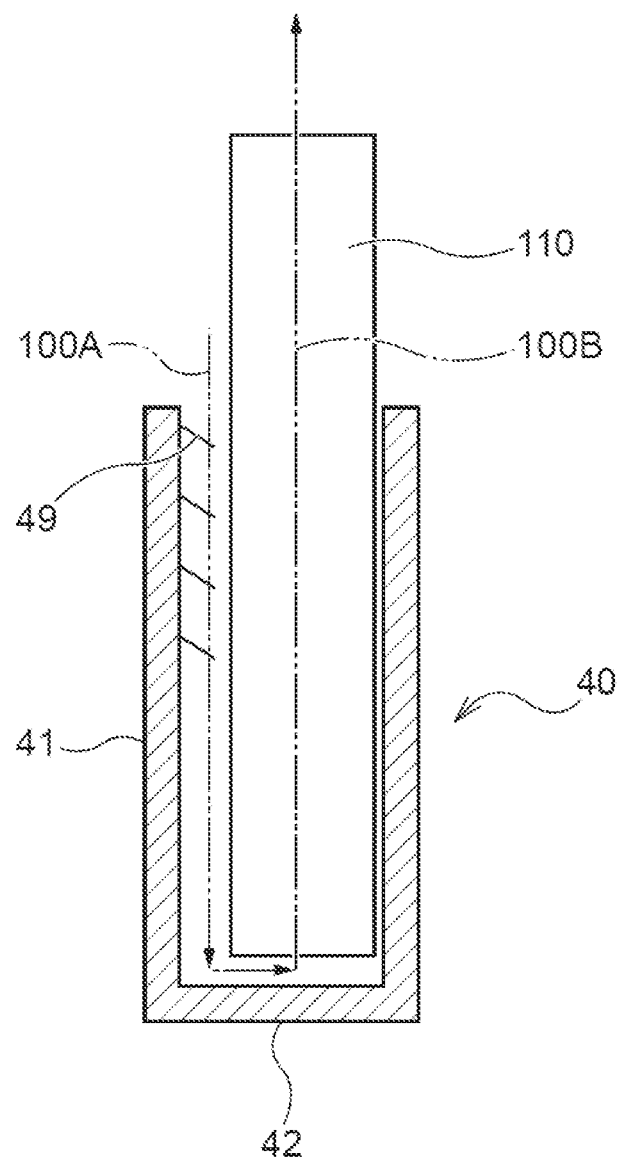
FIG. 30 a diagram for explaining the partition wall 49 according to the additional modification example 3.

FIGS. 28 and 29 are views for explaining the partition wall 49 according to the additional modification example 3. In FIGS. 28 and 29, the partition wall 49 is a plate-like member made of plastic, rubber or the like. The partition wall 49 may be disposed at one place along the longitudinal direction of the second portion 41B or may comprise a plurality of partition walls 49 disposed at a plurality of places along the longitudinal direction of the second portion 41B. The partition walls 49 may be disposed to slope down from attachment positions toward the bottom plate portion 42 as shown in FIG. 30.

The partition wall 49 may have any shape as long as the shape thereof allows a forward airflow from the first end portion 40X toward the second end portion 40Y and blocks a backward thermal vapor stream which flows from the second end portion 40Y toward the first end portion 40X within the first channel 43.

Consequently, when the thermal vapor flows backward from the second end portion 40Y toward the first end portion 40X, the thermal vapor stream hits the partition wall 49 to slow down and is prompted to condense, which reduces the temperature of the thermal vapor. It is preferable that at least one partition wall 49 be disposed adjacently to the first end portion 40X. The partition wall 49 instead may be disposed in the channel forming member 46 shown in FIG. 11.

Figure 31:
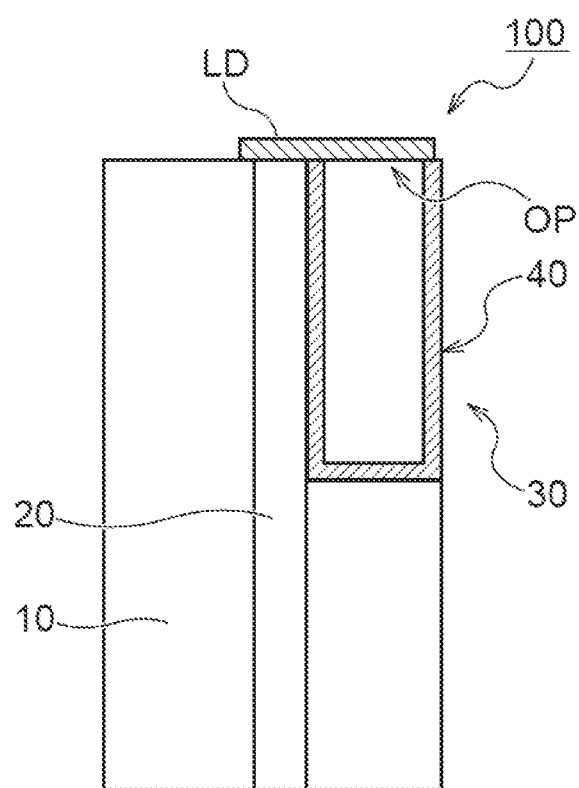
FIG. 31 is a diagram for explaining a lid member LD according to the additional modification example 3.

The following discussion will explain another example of the blocking member. The heater assembly and the flavor inhaler in which the heater assembly is fitted may include the blocking member at a position located away from the container 40. FIG. 31 shows the flavor inhaler 100 provided with the blocking member of the present example. The container 40 of FIG. 31 is fitted in the flavor inhaler 100 of FIG. 31 as a part of the heater assembly 30. The flavor inhaler 100 of FIG. 31 is provided with a movable lid member LD that is intended to cover the opening OP of the container 40. The lid member LD is shiftable between a closed position (second position) in which the lid member LD covers the opening OP of the container 40 when the flavor inhaler 100 is not in use and an open position (first position) in which the lid member LD exposes the opening OP of the container 40 at least partially when the flavor inhaler 100 is in use. The lid member LD shown in FIG. 31 is in the closed position.

Figure 32:
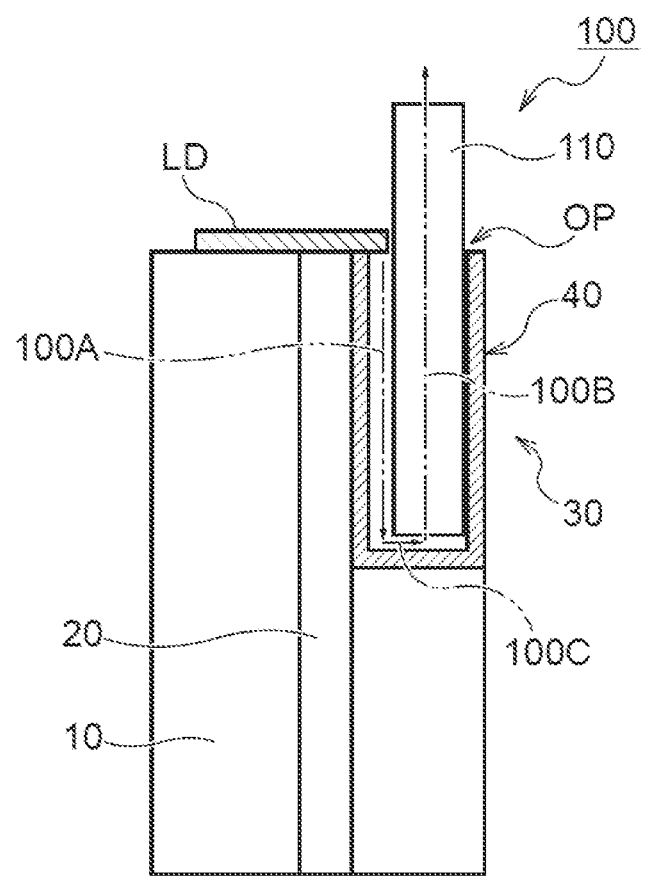
FIG. 32 is a diagram for explaining the lid member LD according to the additional modification example 3.

FIG. 32 shows the flavor inhaler 100 when the lid member LD is in the open position. When the lid member LD is in the open position, the user can insert the flavor generating article 110 from the opening OP into the container 40. According to the present example, the lid member LD in the open position is capable of functioning as the blocking member. More specifically, the lid member LD is configured to cover a part of the opening OP of the container 40 even when the lid member LD is in the open position, to thereby function as the blocking member. The lid member LD thus configured allows the forward airflow of the first channel 43 and at the same time blocks the backward thermal vapor stream as with the partition walls 49 shown in FIGS. 28, 29 and the like. The flavor inhaler 100 may be provided with both the lid member LD and the partition wall 49.

For example, the second portion 41B shown in FIG. 3 may be provided with a backward flow prevention mechanism, instead of the blocking member, which prevents air from flowing backward within the first channel. The backward flow prevention mechanism may be provided at the same place as the partition wall 49 so as to close the entire first channel. The backward flow prevention mechanism is made of, for example, flexible material. The backward flow prevention mechanism allows the forward airflow from the first end portion 40X toward the second end portion 40Y and shuts off the backward thermal vapor stream that flows from the second end portion 40Y toward the first end portion 40X. If the backward flow prevention mechanism is disposed in the channel forming member 46 shown in FIG. 11, a publicly-known check valve may be utilized.

Additional Modification Example 4

An additional modification example 4 of the embodiment will be discussed below. In the additional modification example 4, for example, the cylindrical member 41 and the bottom plate portion 42 of the container 40 shown in FIG. 2 are covered with a heat insulating member 70.

Figure 33:
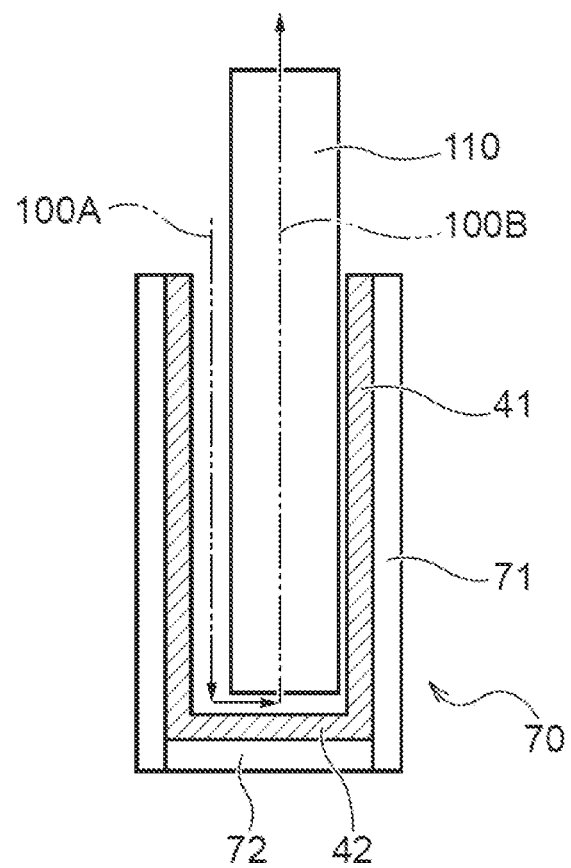
FIG. 33 is a diagram for explaining a thermal insulating member 70 according to an additional modification example 4.

FIG. 33 is a view for explaining the heat insulating member 70 according to the additional modification example 4. In FIG. 33, the heat insulating member 70 may include a first heat insulating member 71 that covers the cylindrical member 41 and a second heat insulating member 72 that covers the bottom plate portion 42. The first heat insulating member 71 and the second heat insulating member 72 are heat insulating members made of heat insulating material, such as vacuum heat insulating material, aerogel, and silicon.

The heat insulating member 70 may be an integrated heat insulating member in which the first heat insulating member 71 that covers the cylindrical member 41 and the second heat insulating member 72 that covers the bottom plate portion 42 continue into each other without a joint. For example, the heat insulating member 70 may be a heat insulating member like a vacuum heat insulating container that covers the cylindrical member 41 and the bottom plate portion 42.

The bottom plate portion 42 of the container 40 is thus covered with the heat insulating member 70, which prevents heat from passing around from the bottom surface of the container 40 to reach the control circuit 20 and the battery 10.

If the heat insulating member 70 is formed of the first heat insulating member 71 and the second heat insulating member 72, the lead wire portion 53 of the heater 50 arranged in the outer peripheral surface of the cylindrical member 41 is allowed to pass through a gap between the first heat insulating member 71 and the second heat insulating member 72.

The first heat insulating member 71 and the second heat insulating member 72 may be heat insulating members made of material having the same thermal conductivity or heat insulating members made of material having different thermal conductivities. In short, heat insulating performance may be equal between the first heat insulating member 71 and the second heat insulating member 72 or higher in either one of the first heat insulating member 71 and the second heat insulating member 72 than the other. According to a mode in which the heater 50 is arranged in the outer peripheral surface of the cylindrical member 41, it is preferable to reinforce the heat insulating performance of the first heat insulating member 71. The second heat insulating member 72 therefore may be lower in heat insulating performance than the first heat insulating member 71.

Additional Modification Example 5

An additional modification example 5 of the embodiment will be now discussed. In the additional modification example 5, for example, the heater 50 and the sensor 60 shown in FIG. 2 are covered with a heat shrinkable tube, now shown.

In other words, the embodiment is so configured that the heat shrinkable tube is placed only at the outside of the heater 50, whereas the additional modification example 5 is so configured that the heat shrinkable tube is placed to cover the cylindrical member 41 and the bottom plate portion 42 of the container 40.

Consequently, when the sensor 60 that detects the puffing action is disposed in the bottom plate portion 42 of the container 40, the heater 50 and the sensor 60 can be fixed together.

Additional Modification Example 6

An additional modification example 6 of the embodiment will be discussed below. In the additional modification example 6, for example, a film is disposed between the cylindrical member 41 and the heater 50 shown in FIG. 2. The film is higher in thermal conductivity than the cylindrical member 41.

The film made of material having high thermal conductivity is a film made of copper or another metal which is higher in thermal conductivity than aluminum or stainless (SUS) of which the cylindrical portion 41 is made.

This makes it possible to homogenize the heat generated in a pattern portion of the heater 50 using the film made of the material having high thermal conductivity and therefore equally heat the outer surface of the flavor generating article 110. This equalizes consumption of components that can generate a flavor included in the flavor generating article 110 and also homogenizes smoke flavor. Furthermore, the flavor generating article 110 is prevented from being heated at a local point, which prevents the aerosol source from becoming depleted at the local point.

Additional Modification Example 7

An additional modification example 7 of the embodiment will be now discussed. In the additional modification example 7, for example, the container 40 shown in FIG. 2 includes the base 80 that is disposed in the bottom plate portion 42 and comes into contact with the distal end portion of the flavor generating article 110 when the flavor generating article 110 is contained in the chamber 40C.

Figure 34:
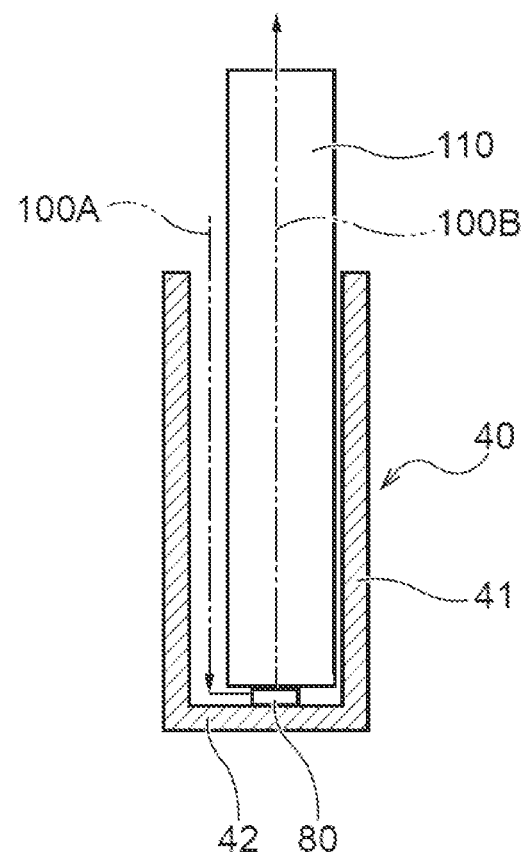
FIG. 34 is a diagram for explaining a base 80 according to an additional modification example 7.

FIG. 34 is a view for explaining the base 80 according to the additional modification example 7. In FIG. 34, the base 80 may have a column-like shape that is formed concentrically with the second portion 41B. The base 80 forms a ring-shaped gap around the base 80. The gap is in communication with the first channel 43 and the second channel 44. That is, the ring-shaped gap corresponds to the third channel 45 that is a channel for the airflow 100C.

The air flowing through the first channel 43 therefore rotates in the ring-shaped gap formed by the base 80 and evenly flows into the flavor generating article 110 from a portion except the base 80 which comes into contact with the distal end portion of the flavor generating article 110. Therefore, the consumption of backing material included in the flavor generating article 110 is equalized, and the smoke flavor is also homogenized.

The invention claimed is:

1. A flavor inhaler comprising:
   a cylindrical portion configured to contain a flavor generating article,
   a temperature sensor disposed on an outer peripheral surface of the cylindrical portion,
   a heat shrinkable tube configured to cover the temperature sensor,
   a heat insulating member located around the cylindrical portion,
   a control unit configured to control heating of the flavor generating article, and
   a battery connected to the control unit,
   wherein the temperature sensor is configured to be used in heating control of the flavor generating article by the control unit.

2. The flavor inhaler according to claim 1, wherein the heat insulating member is configured to cover the cylindrical portion.

3. The flavor inhaler according to claim 1, wherein the heat shrinkable tube is configured to cover the cylindrical portion.

4. The flavor inhaler according to claim 1, further comprising a heater assembly configured to have the cylindrical portion and to heat the flavor generating article,
   wherein the temperature sensor is configured to detect a temperature change caused in the heater assembly.

5. The flavor inhaler according to claim 1, wherein the heat insulating member is made of aerogel.

6. The flavor inhaler according to claim 1, further comprising a movable lid member that is intended to cover an opening of the cylindrical portion.

7. The flavor inhaler according to claim 1, further comprising a lead wire portion configured to continue into a heater for heating the flavor generating article and arranged in an outer peripheral surface of the cylindrical portion.

8. The flavor inhaler according to claim 7, wherein the lead wire portion is configured to pass through a gap between the heat insulating member.

9. The flavor inhaler according to claim 7, wherein the lead wire portion is configured to be connected to the battery through the control unit.

10. The flavor inhaler according to claim 1, wherein the temperature sensor is configured to detect a puffing action.

11. The flavor inhaler according to claim 1, wherein the control unit is configured to control the flavor inhaler to stop heating the flavor generating article if the number of puffing actions exceeds a predetermined value.

12. The flavor inhaler according to claim 1, wherein the cylindrical portion comprises stainless.

13. The flavor inhaler according to claim 1, wherein the cylindrical portion includes an area which is formed at least partially in an inner peripheral surface of the cylindrical portion, the area having higher thermal emissivity than an outer peripheral surface of the cylindrical portion.

14. The flavor inhaler according to claim 1, wherein the control unit is configured to discontinue power supply from the battery when temperature in the flavor inhaler which is measured by the temperature sensor exceeds a predetermined value.

15. A smoking system comprising the flavor inhaler according to claim 1 and the flavor generating article.

* * * * *